United States Patent
Sandmore

(10) Patent No.: US 8,364,220 B2
(45) Date of Patent: Jan. 29, 2013

(54) MEDICAL SENSOR AND TECHNIQUE FOR USING THE SAME

(75) Inventor: Donald Sandmore, Longmont, CO (US)

(73) Assignee: Covidien LP, Mansfield, MA (US)

( * ) Notice: Subject to any disclaimer, the term of this patent is extended or adjusted under 35 U.S.C. 154(b) by 1161 days.

(21) Appl. No.: 12/237,532

(22) Filed: Sep. 25, 2008

(65) Prior Publication Data

US 2010/0076282 A1      Mar. 25, 2010

(51) Int. Cl.
*A61B 5/1455*   (2006.01)
(52) U.S. Cl. .......................... 600/323; 600/344
(58) Field of Classification Search ........... 600/309–344
See application file for complete search history.

(56) References Cited

U.S. PATENT DOCUMENTS

| | | |
|---|---|---|
| 3,721,813 A | 3/1973 | Condon et al. |
| 4,025,733 A | 5/1977 | Klar et al. |
| 4,047,400 A | 9/1977 | Thorneburg |
| 4,462,116 A | 7/1984 | Sanzone et al. |
| 4,499,741 A | 2/1985 | Harris |
| 4,510,938 A | 4/1985 | Jöbsis et al. |
| 4,570,638 A | 2/1986 | Stoddart et al. |
| 4,586,513 A | 5/1986 | Hamaguri |
| 4,603,700 A | 8/1986 | Nichols et al. |
| 4,621,643 A | 11/1986 | New, Jr. et al. |
| 4,653,498 A | 3/1987 | New, Jr. et al. |
| 4,675,919 A | 6/1987 | Heine et al. |
| 4,685,464 A | 8/1987 | Goldberger et al. |
| 4,694,833 A | 9/1987 | Hamaguri |
| 4,697,593 A | 10/1987 | Evans et al. |
| 4,700,708 A | 10/1987 | New, Jr. et al. |
| 4,714,080 A | 12/1987 | Edgar, Jr. et al. |
| 4,714,341 A | 12/1987 | Hamaguri et al. |
| 4,739,757 A | 4/1988 | Edwards |
| 4,759,369 A | 7/1988 | Taylor |
| 4,770,179 A | 9/1988 | New, Jr. et al. |
| 4,773,422 A | 9/1988 | Isaacson et al. |
| 4,775,116 A | 10/1988 | Klein |
| 4,776,339 A | 10/1988 | Schreiber |
| 4,781,195 A | 11/1988 | Martin |

(Continued)

FOREIGN PATENT DOCUMENTS

| | | |
|---|---|---|
| DE | 3516338 | 11/1986 |
| DE | 3703458 | 8/1988 |

(Continued)

OTHER PUBLICATIONS

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summ.

(Continued)

*Primary Examiner* — Eric Winakur
*Assistant Examiner* — Marjan Fardanesh
(74) *Attorney, Agent, or Firm* — Fletcher Yoder

(57) ABSTRACT

According to embodiments, a headcovering hat-based, and/or headband sensor assembly may provide an output to indicate when the sensor experiences abnormal forces or pressure. The sensor assembly may include features to increase the pressure against the tissue to allow the sensor to contact the tissue with sufficient force to obtain accurate measurement, but not so much force as to cause any discomfort for a patient.

18 Claims, 8 Drawing Sheets

U.S. PATENT DOCUMENTS

| | | |
|---|---|---|
| 4,784,162 A | 11/1988 | Ricks et al. |
| 4,796,636 A | 1/1989 | Branstetter et al. |
| 4,800,495 A | 1/1989 | Smith |
| 4,800,885 A | 1/1989 | Johnson |
| 4,802,485 A | 2/1989 | Bowers et al. |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,833,734 A | 5/1989 | Der Estephanian |
| 4,838,279 A | 6/1989 | Fore |
| 4,846,183 A | 7/1989 | Martin |
| 4,848,901 A | 7/1989 | Hood, Jr. |
| 4,854,699 A | 8/1989 | Edgar, Jr. |
| 4,856,116 A | 8/1989 | Sullivan |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,910,804 A | 3/1990 | Lidgren |
| 4,911,167 A | 3/1990 | Corenman et al. |
| 4,913,150 A | 4/1990 | Cheung et al. |
| 4,918,758 A | 4/1990 | Rendina |
| 4,926,867 A | 5/1990 | Kanda et al. |
| 4,927,264 A | 5/1990 | Shiga et al. |
| 4,928,692 A | 5/1990 | Goodman et al. |
| 4,930,888 A | 6/1990 | Feisleben et al. |
| 4,934,372 A | 6/1990 | Corenman et al. |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,972,331 A | 11/1990 | Chance |
| 4,974,591 A | 12/1990 | Awazu et al. |
| 4,977,011 A | 12/1990 | Smith |
| 4,991,234 A | 2/1991 | Greenberg |
| 4,996,975 A | 3/1991 | Nakamura |
| 5,005,374 A | 4/1991 | Spitler |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,040,539 A | 8/1991 | Schmitt et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,080,096 A | 1/1992 | Hooper et al. |
| 5,080,098 A | 1/1992 | Willett et al. |
| 5,084,327 A | 1/1992 | Stengel |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp, Jr. et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker |
| 5,190,038 A | 3/1993 | Polson et al. |
| 5,191,891 A | 3/1993 | Righter |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,214,409 A | 5/1993 | Beigel |
| 5,216,598 A | 6/1993 | Branstetter et al. |
| 5,217,012 A | 6/1993 | Young et al. |
| 5,217,013 A | 6/1993 | Lewis et al. |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,241,300 A | 8/1993 | Buschmann |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Friedman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,567 A | 12/1993 | Aung et al. |
| 5,273,036 A | 12/1993 | Kronberg et al. |
| 5,275,159 A | 1/1994 | Griebel |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,295,490 A | 3/1994 | Dodakian |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Friedman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Brianigan |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,008 A | 9/1994 | Bornn et al. |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,798 A | 10/1994 | Sieben |
| 5,353,799 A | 10/1994 | Chance |
| 5,354,979 A | 10/1994 | Adelson et al. |

| Patent No. | Date | Inventor(s) |
|---|---|---|
| 5,355,880 A | 10/1994 | Thomas et al. |
| 5,355,882 A | 10/1994 | Ukawa et al. |
| 5,357,953 A | 10/1994 | Merrick et al. |
| 5,361,758 A | 11/1994 | Hall et al. |
| 5,365,066 A | 11/1994 | Krueger, Jr. et al. |
| 5,368,025 A | 11/1994 | Young et al. |
| 5,368,026 A | 11/1994 | Swedlow et al. |
| 5,368,224 A | 11/1994 | Richardson et al. |
| 5,368,562 A | 11/1994 | Blomquist et al. |
| 5,372,136 A | 12/1994 | Steuer et al. |
| 5,377,675 A | 1/1995 | Ruskewicz et al. |
| 5,383,874 A | 1/1995 | Jackson et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,398,689 A | 3/1995 | Connor et al. |
| 5,400,267 A | 3/1995 | Denen et al. |
| 5,402,777 A | 4/1995 | Warring et al. |
| 5,405,269 A | 4/1995 | Stupecky |
| 5,405,614 A | 4/1995 | D'Angelo et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,415,166 A | 5/1995 | Imran |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,437,634 A | 8/1995 | Amano |
| 5,438,986 A | 8/1995 | Disch et al. |
| 5,444,254 A | 8/1995 | Thomson |
| 5,448,991 A | 9/1995 | Polson et al. |
| 5,451,763 A | 9/1995 | Pickett et al. |
| 5,452,717 A | 9/1995 | Brianigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,483,646 A | 1/1996 | Uchikoga |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,528,519 A | 6/1996 | Ohkura et al. |
| 5,529,064 A | 6/1996 | Rall et al. |
| 5,533,507 A | 7/1996 | Potratz et al. |
| 5,546,955 A | 8/1996 | Wilk |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,562,718 A | 10/1996 | Palermo |
| 5,564,108 A | 10/1996 | Hunsaker et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,592,408 A | 1/1997 | Keskin et al. |
| 5,595,176 A | 1/1997 | Yamaura |
| 5,596,986 A | 1/1997 | Goldfarb |
| 5,596,987 A | 1/1997 | Chance |
| 5,611,337 A | 3/1997 | Bukta |
| 5,617,852 A | 4/1997 | MacGregor |
| 5,617,865 A | 4/1997 | Palczewska et al. |
| 5,617,866 A | 4/1997 | Marian, Jr. |
| 5,619,992 A | 4/1997 | Guthrie et al. |
| 5,626,140 A | 5/1997 | Feldman et al. |
| 5,627,323 A | 5/1997 | Stern |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,634,466 A | 6/1997 | Gruner |
| 5,638,593 A | 6/1997 | Gerhardt et al. |
| 5,638,818 A | 6/1997 | Diab et al. |
| 5,640,953 A | 6/1997 | Bishop et al. |
| 5,645,060 A | 7/1997 | Yorkey et al. |
| 5,645,440 A | 7/1997 | Tobler et al. |
| 5,645,586 A | 7/1997 | Meltzer |
| 5,646,416 A | 7/1997 | Van De Velde |
| 5,660,567 A | 8/1997 | Nierlich et al. |
| 5,662,105 A | 9/1997 | Tien |
| 5,662,106 A | 9/1997 | Swedlow et al. |
| 5,666,952 A | 9/1997 | Fuse et al. |
| 5,671,529 A | 9/1997 | Nelson |
| 5,671,750 A | 9/1997 | Shinoda |
| 5,673,692 A | 10/1997 | Schulze et al. |
| 5,673,693 A | 10/1997 | Solenberger |
| 5,673,708 A | 10/1997 | Athanasiou et al. |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,681,285 A | 10/1997 | Ford et al. |
| 5,683,434 A | 11/1997 | Archer |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Kuenstner |
| 5,692,505 A | 12/1997 | Fouts |
| 5,697,363 A | 12/1997 | Hart |
| 5,697,367 A | 12/1997 | Lewis et al. |
| 5,701,894 A | 12/1997 | Cherry et al. |
| 5,706,820 A | 1/1998 | Hossack et al. |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,731,582 A | 3/1998 | West |
| 5,732,475 A | 3/1998 | Sacks et al. |
| D393,830 S | 4/1998 | Tobler et al. |
| 5,738,612 A | 4/1998 | Tsuda |
| 5,743,260 A | 4/1998 | Chung et al. |
| 5,743,263 A | 4/1998 | Baker, Jr. |
| 5,743,856 A | 4/1998 | Oka et al. |
| 5,743,857 A | 4/1998 | Shinoda et al. |
| 5,746,206 A | 5/1998 | Mannheimer |
| 5,746,697 A | 5/1998 | Swedlow et al. |
| 5,752,913 A | 5/1998 | Oka |
| 5,752,914 A | 5/1998 | DeLonzor et al. |
| 5,752,920 A | 5/1998 | Ogura et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |

| Patent | Date | Name |
|---|---|---|
| 5,769,785 A | 6/1998 | Diab et al. |
| 5,772,587 A | 6/1998 | Gratton et al. |
| 5,772,601 A | 6/1998 | Oka et al. |
| 5,774,213 A | 6/1998 | Trebino et al. |
| 5,776,058 A | 7/1998 | Levinson et al. |
| 5,776,059 A | 7/1998 | Kaestle |
| 5,776,071 A | 7/1998 | Inukai et al. |
| 5,779,630 A | 7/1998 | Fein et al. |
| 5,779,631 A | 7/1998 | Chance |
| 5,779,639 A | 7/1998 | Yeung |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,786,592 A | 7/1998 | Hök |
| 5,790,729 A | 8/1998 | Pologe et al. |
| 5,791,347 A | 8/1998 | Flaherty et al. |
| 5,791,348 A | 8/1998 | Aung et al. |
| 5,792,052 A | 8/1998 | Isaacson et al. |
| 5,792,058 A | 8/1998 | Lee et al. |
| 5,795,292 A | 8/1998 | Lewis et al. |
| 5,797,841 A | 8/1998 | Delonzor et al. |
| 5,800,348 A | 9/1998 | Kaestle |
| 5,800,349 A | 9/1998 | Isaacson et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,012 A | 10/1998 | Hacskaylo |
| 5,823,950 A | 10/1998 | Diab et al. |
| 5,823,952 A | 10/1998 | Levinson et al. |
| 5,826,277 A | 10/1998 | McConville |
| 5,827,182 A | 10/1998 | Raley et al. |
| 5,830,135 A | 11/1998 | Bosque et al. |
| 5,830,136 A | 11/1998 | Delonzor et al. |
| 5,830,137 A | 11/1998 | Scharf |
| 5,830,148 A | 11/1998 | Inukai et al. |
| 5,830,149 A | 11/1998 | Oka et al. |
| 5,833,602 A | 11/1998 | Osemwota |
| 5,836,887 A | 11/1998 | Oka et al. |
| 5,839,439 A | 11/1998 | Nierlich et al. |
| RE36,000 E | 12/1998 | Swedlow et al. |
| 5,842,979 A | 12/1998 | Jarman |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,857,974 A | 1/1999 | Eberle et al. |
| 5,860,919 A | 1/1999 | Kiani-Azarbayjany et al. |
| 5,860,932 A | 1/1999 | Goto et al. |
| 5,860,957 A | 1/1999 | Jacobsen et al. |
| 5,865,736 A | 2/1999 | Baker, Jr. et al. |
| 5,868,133 A | 2/1999 | DeVries et al. |
| 5,870,626 A | 2/1999 | Lebeau |
| 5,871,442 A | 2/1999 | Madarasz et al. |
| 5,872,713 A | 2/1999 | Douglas et al. |
| 5,873,821 A | 2/1999 | Chance et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,895,359 A | 4/1999 | Peel |
| 5,902,235 A | 5/1999 | Lewis et al. |
| 5,906,581 A | 5/1999 | Tsuda |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,931,790 A | 8/1999 | Peel |
| 5,931,791 A | 8/1999 | Saltzstein et al. |
| 5,934,277 A | 8/1999 | Mortz |
| 5,934,925 A | 8/1999 | Tobler et al. |
| 5,936,539 A | 8/1999 | Fuchs |
| 5,940,182 A | 8/1999 | Lepper, Jr. et al. |
| 5,947,905 A | 9/1999 | Hadjicostis |
| 5,954,053 A | 9/1999 | Chance et al. |
| 5,954,644 A | 9/1999 | Dettling et al. |
| 5,957,850 A | 9/1999 | Marian, Jr. et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,980,464 A | 11/1999 | Tsuda |
| 5,983,122 A | 11/1999 | Jarman et al. |
| 5,983,129 A | 11/1999 | Cowan et al. |
| 5,987,343 A | 11/1999 | Kinast |
| 5,987,351 A | 11/1999 | Chance |
| 5,991,648 A | 11/1999 | Levin |
| 5,995,077 A | 11/1999 | Wilcox et al. |
| 5,995,855 A | 11/1999 | Kiani et al. |
| 5,995,856 A | 11/1999 | Mannheimer et al. |
| 5,995,857 A | 11/1999 | Toomim et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,007,492 A | 12/1999 | Goto et al. |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,320 A | 2/2000 | Ogura et al. |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,027,453 A | 2/2000 | Miwa et al. |
| 6,030,351 A | 2/2000 | Schmidt et al. |
| 6,031,603 A | 2/2000 | Fine et al. |
| 6,035,223 A | 3/2000 | Baker, Jr. |
| 6,036,642 A | 3/2000 | Diab et al. |
| 6,036,651 A | 3/2000 | Inukai et al. |
| 6,041,247 A | 3/2000 | Weckstrom et al. |
| 6,044,283 A | 3/2000 | Fein et al. |
| 6,047,201 A | 4/2000 | Jackson |
| 6,047,203 A | 4/2000 | Sackner et al. |
| 6,049,958 A | 4/2000 | Eberle et al. |
| 6,050,951 A | 4/2000 | Friedman et al. |
| 6,052,619 A | 4/2000 | John |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,833 A | 6/2000 | Hueber |
| 6,081,735 A | 6/2000 | Diab et al. |

| | | |
|---|---|---|
| 6,081,742 A | 6/2000 | Amano et al. |
| 6,083,157 A | 7/2000 | Noller |
| 6,083,172 A | 7/2000 | Baker, Jr. et al. |
| 6,084,380 A | 7/2000 | Burton |
| 6,085,752 A | 7/2000 | Kehr et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,106,780 A | 8/2000 | Douglas et al. |
| 6,112,107 A | 8/2000 | Hannula |
| 6,113,541 A | 9/2000 | Dias et al. |
| 6,115,621 A | 9/2000 | Chin |
| 6,118,382 A | 9/2000 | Hibbs et al. |
| 6,122,535 A | 9/2000 | Kaestle et al. |
| 6,133,994 A | 10/2000 | Mathews et al. |
| 6,134,459 A | 10/2000 | Roberts et al. |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,150,951 A | 11/2000 | Olejniczak |
| 6,151,107 A | 11/2000 | Schöllerman et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,162,188 A | 12/2000 | Barnea |
| 6,163,715 A | 12/2000 | Larsen et al. |
| 6,165,005 A | 12/2000 | Mills et al. |
| 6,165,173 A | 12/2000 | Kamdar et al. |
| 6,171,258 B1 | 1/2001 | Katakasoglu et al. |
| 6,173,196 B1 | 1/2001 | Delonzor et al. |
| 6,178,343 B1 | 1/2001 | Bindszus et al. |
| 6,179,786 B1 | 1/2001 | Young |
| 6,181,958 B1 | 1/2001 | Steuer et al. |
| 6,181,959 B1 | 1/2001 | Schöllerman et al. |
| 6,184,521 B1 | 2/2001 | Coffin, IV et al. |
| 6,186,953 B1 | 2/2001 | Narimatsu |
| 6,186,954 B1 | 2/2001 | Narimatsu |
| 6,188,470 B1 | 2/2001 | Grace |
| 6,190,325 B1 | 2/2001 | Narimatsu |
| 6,192,260 B1 | 2/2001 | Chance |
| 6,195,575 B1 | 2/2001 | Levinson |
| 6,196,974 B1 | 3/2001 | Miwa |
| 6,198,951 B1 | 3/2001 | Kosuda et al. |
| 6,198,952 B1 | 3/2001 | Miesel |
| 6,199,550 B1 | 3/2001 | Wiesmann et al. |
| 6,206,830 B1 | 3/2001 | Diab et al. |
| 6,209,144 B1 | 4/2001 | Carter |
| 6,213,952 B1 | 4/2001 | Finarov et al. |
| 6,216,021 B1 | 4/2001 | Franceschini et al. |
| 6,217,523 B1 | 4/2001 | Amano et al. |
| 6,222,189 B1 | 4/2001 | Misner et al. |
| 6,223,063 B1 | 4/2001 | Chaiken et al. |
| 6,226,539 B1 | 5/2001 | Potratz |
| 6,226,540 B1 | 5/2001 | Bernreuter |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,241,680 B1 | 6/2001 | Miwa |
| 6,248,083 B1 | 6/2001 | Smith et al. |
| 6,251,076 B1 | 6/2001 | Hovland et al. |
| 6,251,080 B1 | 6/2001 | Henkin et al. |
| 6,251,081 B1 | 6/2001 | Narimatsu |
| 6,251,113 B1 | 6/2001 | Appelbaum et al. |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,282,450 B1 | 8/2001 | Hartlaub et al. |
| 6,283,922 B1 | 9/2001 | Goto et al. |
| 6,285,894 B1 | 9/2001 | Oppelt et al. |
| 6,285,895 B1 | 9/2001 | Ristolainen et al. |
| 6,285,896 B1 | 9/2001 | Tobler et al. |
| 6,298,252 B1 | 10/2001 | Kovach et al. |
| 6,306,076 B1 | 10/2001 | Gill |
| 6,308,089 B1 | 10/2001 | von der Ruhr et al. |
| 6,321,100 B1 | 11/2001 | Parker |
| 6,322,516 B1 | 11/2001 | Masuda et al. |
| 6,330,468 B1 | 12/2001 | Scharf |
| 6,334,065 B1 | 12/2001 | Al-Ali et al. |
| 6,339,715 B1 | 1/2002 | Bahr et al. |
| 6,343,223 B1 | 1/2002 | Chin et al. |
| 6,343,224 B1 | 1/2002 | Parker |
| 6,346,886 B1 | 2/2002 | De La Huerga |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,362,622 B1 | 3/2002 | Stauber et al. |
| 6,363,269 B1 | 3/2002 | Hanna et al. |
| 6,368,282 B1 | 4/2002 | Oka et al. |
| 6,370,408 B1 | 4/2002 | Merchant et al. |
| 6,370,409 B1 | 4/2002 | Chung et al. |
| 6,370,411 B1 | 4/2002 | Osadchy et al. |
| 6,374,129 B1 | 4/2002 | Chin et al. |
| 6,377,829 B1 | 4/2002 | Al-Ali |
| 6,381,479 B1 | 4/2002 | Norris |
| 6,381,480 B1 | 4/2002 | Stoddar et al. |
| 6,381,481 B1 | 4/2002 | Levendowski et al. |
| 6,385,471 B1 | 5/2002 | Mortz |
| 6,385,486 B1 | 5/2002 | John et al. |
| 6,385,821 B1 | 5/2002 | Modgil et al. |
| 6,387,092 B1 | 5/2002 | Burnside et al. |
| 6,388,240 B2 | 5/2002 | Schulz et al. |
| 6,393,310 B1 | 5/2002 | Kuenster |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,402,690 B1 | 6/2002 | Rhee et al. |
| 6,405,075 B1 | 6/2002 | Levin |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,416,471 B1 | 7/2002 | Kumar et al. |
| 6,416,474 B1 | 7/2002 | Penner et al. |
| 6,417,774 B1 | 7/2002 | Hibbs et al. |
| 6,419,671 B1 | 7/2002 | Lemberg |
| 6,421,549 B1 | 7/2002 | Jacques |
| 6,423,010 B1 | 7/2002 | Friedman et al. |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,432,050 B1 | 8/2002 | Porat et al. |
| 6,434,408 B1 | 8/2002 | Heckel et al. |
| 6,438,399 B1 | 8/2002 | Kurth |
| 6,449,501 B1 | 9/2002 | Reuss |
| 6,450,168 B1 | 9/2002 | Nguyen |
| 6,450,957 B1 | 9/2002 | Yoshimi et al. |
| 6,450,981 B1 | 9/2002 | Shabty et al. |
| 6,453,183 B1 | 9/2002 | Walker |
| 6,453,184 B1 | 9/2002 | Hyogo et al. |
| 6,454,708 B1 | 9/2002 | Ferguson et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |

| Patent | Date | Name |
|---|---|---|
| 6,466,809 B1 | 10/2002 | Riley |
| 6,468,241 B1 | 10/2002 | Gelfand et al. |
| 6,470,199 B1 | 10/2002 | Kopotic et al. |
| 6,470,200 B2 | 10/2002 | Walker et al. |
| 6,470,279 B1 | 10/2002 | Samsoondar |
| 6,480,729 B2 | 11/2002 | Stone |
| 6,480,762 B1 | 11/2002 | Uchikubo et al. |
| 6,490,466 B1 | 12/2002 | Fein et al. |
| 6,491,638 B2 | 12/2002 | Oka |
| 6,491,639 B1 | 12/2002 | Turcott |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,503,087 B1 | 1/2003 | Eggert et al. |
| 6,503,204 B1 | 1/2003 | Sumanaweera et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,511,478 B1 | 1/2003 | Burnside et al. |
| 6,512,937 B2 | 1/2003 | Blank et al. |
| 6,515,273 B2 | 2/2003 | Al-Ali |
| 6,516,289 B2 | 2/2003 | David |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,524,257 B2 | 2/2003 | Ogura |
| 6,525,386 B1 | 2/2003 | Mills et al. |
| 6,526,300 B1 | 2/2003 | Kiani et al. |
| 6,526,301 B2 | 2/2003 | Larsen et al. |
| 6,526,309 B1 | 2/2003 | Chance |
| 6,526,970 B1 | 3/2003 | DeVries et al. |
| 6,527,725 B1 | 3/2003 | Inukai et al. |
| 6,527,726 B2 | 3/2003 | Goto et al. |
| 6,535,765 B1 | 3/2003 | Amely-Velez et al. |
| 6,537,220 B1 | 3/2003 | Friemel et al. |
| 6,541,756 B2 | 4/2003 | Schulz et al. |
| 6,542,081 B2 | 4/2003 | Torch |
| 6,542,764 B1 | 4/2003 | Al-Ali et al. |
| 6,546,267 B1 | 4/2003 | Sugiura et al. |
| 6,547,742 B2 | 4/2003 | Oka et al. |
| 6,547,743 B2 | 4/2003 | Brydon |
| 6,551,252 B2 | 4/2003 | Sackner et al. |
| 6,553,241 B2 | 4/2003 | Mannheimer et al. |
| 6,553,242 B1 | 4/2003 | Sarussi |
| 6,553,243 B2 | 4/2003 | Gurley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,575,902 B1 | 6/2003 | Burton |
| 6,575,904 B2 | 6/2003 | Nagai et al. |
| 6,580,086 B1 | 6/2003 | Schulz et al. |
| 6,582,371 B2 | 6/2003 | Miller |
| 6,582,374 B2 | 6/2003 | Yokozeki |
| 6,584,336 B1 | 6/2003 | Ali et al. |
| 6,584,356 B2 | 6/2003 | Wassmund et al. |
| 6,587,703 B2 | 7/2003 | Cheng et al. |
| 6,587,704 B1 | 7/2003 | Fine et al. |
| 6,589,171 B2 | 7/2003 | Keirsbilck |
| 6,589,172 B2 | 7/2003 | Williams et al. |
| 6,589,183 B2 | 7/2003 | Yokozeki |
| 6,589,189 B2 | 7/2003 | Meyerson et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,605,038 B1 | 8/2003 | Teller et al. |
| 6,606,510 B2 | 8/2003 | Swedlow et al. |
| 6,606,511 B1 | 8/2003 | Ali et al. |
| 6,606,512 B2 | 8/2003 | Muz et al. |
| 6,606,993 B1 | 8/2003 | Wiesmann et al. |
| 6,611,793 B1 | 8/2003 | Burnside et al. |
| 6,615,064 B1 | 9/2003 | Aldrich |
| 6,615,065 B1 | 9/2003 | Barrett et al. |
| 6,618,602 B2 | 9/2003 | Levin et al. |
| 6,622,034 B1 | 9/2003 | Gorski et al. |
| 6,628,975 B1 | 9/2003 | Fein et al. |
| 6,631,281 B1 | 10/2003 | Kästle |
| 6,635,048 B1 | 10/2003 | Ullestad et al. |
| 6,640,116 B2 | 10/2003 | Diab |
| 6,643,530 B2 | 11/2003 | Diab et al. |
| 6,643,531 B1 | 11/2003 | Katarow |
| 6,645,154 B2 | 11/2003 | Oka |
| 6,645,155 B2 | 11/2003 | Inukai et al. |
| 6,647,279 B2 | 11/2003 | Pologe |
| 6,647,280 B2 | 11/2003 | Bahr et al. |
| 6,650,917 B2 | 11/2003 | Diab et al. |
| 6,650,918 B2 | 11/2003 | Terry |
| 6,653,557 B2 | 11/2003 | Wolf et al. |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kainl et al. |
| 6,658,277 B2 | 12/2003 | Wassermann |
| 6,662,033 B2 | 12/2003 | Casciani et al. |
| 6,665,551 B1 | 12/2003 | Suzuki |
| 6,666,860 B1 | 12/2003 | Takahashi |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,671,545 B2 | 12/2003 | Fincke |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,694,160 B2 | 2/2004 | Chin |
| 6,695,806 B2 | 2/2004 | Gelfand et al. |
| 6,697,653 B2 | 2/2004 | Hanna |
| 6,697,655 B2 | 2/2004 | Sueppel et al. |
| 6,697,656 B1 | 2/2004 | Al-Ali |
| 6,697,658 B2 | 2/2004 | Al-Ali |
| RE38,476 E | 3/2004 | Diab et al. |
| 6,699,194 B1 | 3/2004 | Diab et al. |
| 6,699,199 B2 | 3/2004 | Asada et al. |
| 6,700,497 B2 | 3/2004 | Hibbs et al. |
| 6,701,170 B2 | 3/2004 | Stetson |
| 6,702,752 B2 | 3/2004 | Dekker |
| 6,704,601 B1 | 3/2004 | Amely-Velez et al. |
| 6,707,257 B2 | 3/2004 | Norris |
| 6,708,048 B1 | 3/2004 | Chance |
| 6,708,049 B1 | 3/2004 | Berson et al. |
| 6,709,402 B2 | 3/2004 | Dekker |
| 6,711,424 B1 | 3/2004 | Fine et al. |
| 6,711,425 B1 | 3/2004 | Reuss |
| 6,712,767 B2 | 3/2004 | Hossack et al. |
| 6,714,803 B1 | 3/2004 | Mortz |
| 6,714,804 B2 | 3/2004 | Al-Ali et al. |
| 6,714,805 B2 | 3/2004 | Jeon et al. |
| RE38,492 E | 4/2004 | Diab et al. |
| 6,719,686 B2 | 4/2004 | Coakley et al. |
| 6,719,705 B2 | 4/2004 | Mills |
| 6,720,734 B2 | 4/2004 | Norris |
| 6,721,584 B2 | 4/2004 | Baker, Jr. et al. |
| 6,721,585 B1 | 4/2004 | Parker |
| 6,721,602 B2 | 4/2004 | Engmark et al. |
| 6,725,074 B1 | 4/2004 | Kästle |
| 6,725,075 B2 | 4/2004 | Al-Ali |
| 6,726,327 B2 | 4/2004 | Torrey et al. |
| 6,731,963 B2 | 5/2004 | Finarov et al. |
| 6,731,967 B1 | 5/2004 | Turcott |

| | | |
|---|---|---|
| 6,735,459 B2 | 5/2004 | Parker |
| 6,736,759 B1 | 5/2004 | Stubbs et al. |
| 6,736,786 B1 | 5/2004 | Shabty et al. |
| 6,743,173 B2 | 6/2004 | Penner et al. |
| 6,743,202 B2 | 6/2004 | Hirschman et al. |
| 6,745,060 B2 | 6/2004 | Diab et al. |
| 6,745,061 B1 | 6/2004 | Hicks et al. |
| 6,748,253 B2 | 6/2004 | Norris et al. |
| 6,748,254 B2 | 6/2004 | O'Neill et al. |
| 6,748,262 B2 | 6/2004 | Harada et al. |
| 6,749,567 B2 | 6/2004 | Davis |
| 6,754,515 B1 | 6/2004 | Pologe |
| 6,754,516 B2 | 6/2004 | Mannheimer |
| 6,755,789 B2 | 6/2004 | Stringer et al. |
| 6,758,808 B2 | 7/2004 | Paul |
| 6,760,607 B2 | 7/2004 | Al-Ali |
| 6,760,609 B2 | 7/2004 | Jacques |
| 6,760,610 B2 | 7/2004 | Tschupp et al. |
| 6,763,255 B2 | 7/2004 | Delonzor et al. |
| 6,763,256 B2 | 7/2004 | Kimball et al. |
| 6,767,330 B2 | 7/2004 | Lavery |
| 6,770,028 B1 | 8/2004 | Ali et al. |
| 6,771,994 B2 | 8/2004 | Kiani et al. |
| 6,773,397 B2 | 8/2004 | Kelly |
| 6,776,758 B2 | 8/2004 | Peszynski et al. |
| 6,778,923 B2 | 8/2004 | Norris et al. |
| 6,779,257 B2 | 8/2004 | Kiepen et al. |
| 6,780,158 B2 | 8/2004 | Yarita |
| 6,785,568 B2 | 8/2004 | Chance |
| 6,792,300 B1 | 9/2004 | Diab et al. |
| 6,793,654 B2 | 9/2004 | Lemberg |
| 6,796,946 B2 | 9/2004 | Ogura et al. |
| 6,801,797 B2 | 10/2004 | Mannheimer et al. |
| 6,801,798 B2 | 10/2004 | Geddes et al. |
| 6,801,799 B2 | 10/2004 | Mendelson |
| 6,801,802 B2 | 10/2004 | Sitzman et al. |
| 6,802,812 B1 | 10/2004 | Walker et al. |
| 6,804,543 B2 | 10/2004 | Miller et al. |
| 6,804,558 B2 | 10/2004 | Haller et al. |
| 6,805,673 B2 | 10/2004 | Dekker |
| 6,808,496 B2 | 10/2004 | Oka et al. |
| 6,810,277 B2 | 10/2004 | Edgar, Jr. et al. |
| 6,811,538 B2 | 11/2004 | Westbrook et al. |
| 6,813,511 B2 | 11/2004 | Diab et al. |
| 6,813,551 B2 | 11/2004 | Diab et al. |
| 6,816,741 B2 | 11/2004 | Diab |
| 6,819,950 B2 | 11/2004 | Mills |
| 6,822,564 B2 | 11/2004 | Al-Ali |
| 6,824,520 B2 | 11/2004 | Orr et al. |
| 6,825,619 B2 | 11/2004 | Norris |
| 6,826,419 B2 | 11/2004 | Diab et al. |
| 6,827,688 B2 | 12/2004 | Goto et al. |
| 6,829,003 B2 | 12/2004 | Takami |
| 6,829,496 B2 | 12/2004 | Nagai et al. |
| 6,830,711 B2 | 12/2004 | Mills et al. |
| 6,832,987 B2 | 12/2004 | David et al. |
| 6,836,679 B2 | 12/2004 | Baker, Jr. et al. |
| 6,839,579 B1 | 1/2005 | Chin |
| 6,839,580 B2 | 1/2005 | Zonios et al. |
| 6,839,582 B2 | 1/2005 | Heckel |
| 6,839,659 B2 | 1/2005 | Tarassenko et al. |
| 6,842,635 B1 | 1/2005 | Parker |
| 6,842,722 B2 | 1/2005 | David |
| 6,845,256 B2 | 1/2005 | Chin et al. |
| 6,847,294 B1 | 1/2005 | Lin et al. |
| 6,849,074 B2 | 2/2005 | Chen et al. |
| 6,850,787 B2 | 2/2005 | Weber et al. |
| 6,850,788 B2 | 2/2005 | Al-Ali |
| 6,850,789 B2 | 2/2005 | Schweitzer, Jr. et al. |
| 6,853,304 B2 | 2/2005 | Reisman et al. |
| 6,861,639 B2 | 3/2005 | Al-Ali |
| 6,863,652 B2 | 3/2005 | Huang et al. |
| 6,865,407 B2 | 3/2005 | Kimball et al. |
| 6,870,479 B2 | 3/2005 | Gabriel |
| 6,875,176 B2 | 4/2005 | Mourad et al. |
| 6,877,511 B2 | 4/2005 | DeVries et al. |
| 6,879,850 B2 | 4/2005 | Kimball |
| 6,882,874 B2 | 4/2005 | Huiku |
| 6,889,153 B2 | 5/2005 | Dietiker |
| 6,893,400 B2 | 5/2005 | Kawaguchi et al. |
| 6,898,299 B1 | 5/2005 | Brooks |
| 6,898,452 B2 | 5/2005 | Al-Ali et al. |
| 6,899,682 B2 | 5/2005 | Eberle et al. |
| 6,899,684 B2 | 5/2005 | Mault et al. |
| 6,904,124 B2 | 6/2005 | Staver et al. |
| 6,907,284 B2 | 6/2005 | Hamilton et al. |
| 6,909,912 B2 | 6/2005 | Melker |
| 6,911,027 B1 | 6/2005 | Edwards et al. |
| 6,912,413 B2 | 6/2005 | Rantala et al. |
| 6,915,167 B2 | 7/2005 | Splett et al. |
| 6,916,289 B2 | 7/2005 | Schnall |
| 6,920,345 B2 | 7/2005 | Al-Ali et al. |
| 6,921,198 B2 | 7/2005 | Gruszecki et al. |
| 6,923,771 B2 | 8/2005 | Ogura et al. |
| 6,923,776 B2 | 8/2005 | Shabty et al. |
| 6,930,608 B2 | 8/2005 | Grajales et al. |
| 6,931,269 B2 | 8/2005 | Terry |
| 6,934,570 B2 | 8/2005 | Kiani et al. |
| 6,934,571 B2 | 8/2005 | Wiesmann et al. |
| 6,936,011 B2 | 8/2005 | Sheldon |
| 6,938,488 B2 | 9/2005 | Diaz et al. |
| 6,939,307 B1 | 9/2005 | Dunlop |
| 6,939,314 B2 | 9/2005 | Hall et al. |
| 6,941,162 B2 | 9/2005 | Fudge et al. |
| 6,943,881 B2 | 9/2005 | Wang |
| 6,944,498 B2 | 9/2005 | Owens et al. |
| 6,947,781 B2 | 9/2005 | Asada et al. |
| 6,950,687 B2 | 9/2005 | Al-Ali |
| 6,952,870 B2 | 10/2005 | Miller |
| 6,955,650 B2 | 10/2005 | Mault et al. |
| 6,963,767 B2 | 11/2005 | Rantala et al. |
| 6,965,071 B2 | 11/2005 | Watchko et al. |
| 6,971,580 B2 | 12/2005 | Zhu et al. |
| 6,971,790 B2 | 12/2005 | Quinn et al. |
| 6,979,329 B2 | 12/2005 | Burnside et al. |
| 6,983,178 B2 | 1/2006 | Fine et al. |
| 6,985,763 B2 | 1/2006 | Boas et al. |
| 6,985,764 B2 | 1/2006 | Mason et al. |
| 6,990,371 B2 | 1/2006 | Powers et al. |
| 6,990,426 B2 | 1/2006 | Yoon et al. |
| 6,992,751 B2 | 1/2006 | Okita et al. |
| 6,992,772 B2 | 1/2006 | Block et al. |
| 6,993,371 B2 | 1/2006 | Kiani et al. |
| 6,993,372 B2 | 1/2006 | Fine et al. |
| 6,995,665 B2 | 2/2006 | Appelt et al. |
| 6,996,427 B2 | 2/2006 | Ali et al. |
| 7,001,334 B2 | 2/2006 | Reed et al. |
| 7,003,338 B2 | 2/2006 | Weber et al. |
| 7,003,339 B2 | 2/2006 | Diab et al. |
| 7,006,855 B1 | 2/2006 | Sarussi |
| 7,006,856 B2 | 2/2006 | Baker, Jr. et al. |
| 7,016,715 B2 | 3/2006 | Stetson |
| 7,017,420 B2 | 3/2006 | Kalvesten et al. |
| 7,018,338 B2 | 3/2006 | Vetter et al. |
| 7,019,392 B2 | 3/2006 | Iwasaki |
| 7,020,507 B2 | 3/2006 | Scharf et al. |
| 7,020,508 B2 | 3/2006 | Stivoric et al. |
| 7,024,233 B2 | 4/2006 | Ali et al. |
| 7,024,235 B2 | 4/2006 | Melker et al. |
| 7,025,728 B2 | 4/2006 | Ito et al. |
| 7,027,849 B2 | 4/2006 | Al-Ali et al. |
| 7,027,850 B2 | 4/2006 | Wasserman |
| 7,027,871 B2 | 4/2006 | Burnes et al. |
| 7,033,316 B2 | 4/2006 | Takahashi |
| 7,035,697 B1 | 4/2006 | Brown |
| 7,039,449 B2 | 5/2006 | Al-Ali |
| 7,041,121 B1 | 5/2006 | Williams et al. |
| 7,043,289 B2 | 5/2006 | Fine et al. |
| 7,047,054 B2 | 5/2006 | Benni |
| 7,047,055 B2 | 5/2006 | Boaz et al. |
| 7,047,056 B2 | 5/2006 | Hannula et al. |
| 7,048,687 B1 | 5/2006 | Reuss et al. |
| 7,052,509 B2 | 5/2006 | Lennox |
| 7,060,035 B2 | 6/2006 | Wasserman et al. |
| 7,062,307 B2 | 6/2006 | Norris et al. |
| 7,063,669 B2 | 6/2006 | Brawner et al. |
| 7,067,893 B2 | 6/2006 | Mills et al. |
| 7,072,701 B2 | 7/2006 | Chen et al. |

| | | |
|---|---|---|
| 7,072,702 B2 | 7/2006 | Edgar, Jr. et al. |
| 7,079,036 B2 | 7/2006 | Cooper et al. |
| 7,079,880 B2 | 7/2006 | Stetson |
| 7,081,128 B2 | 7/2006 | Hart et al. |
| 7,085,597 B2 | 8/2006 | Fein et al. |
| 7,087,023 B2 | 8/2006 | Daft et al. |
| 7,089,061 B2 | 8/2006 | Grey |
| 7,096,052 B2 | 8/2006 | Mason et al. |
| 7,096,054 B2 | 8/2006 | Abdul-Hafiz et al. |
| 7,097,621 B2 | 8/2006 | Narimatsu et al. |
| 7,107,088 B2 | 9/2006 | Aceti |
| 7,107,706 B1 | 9/2006 | Bailey |
| 7,108,659 B2 | 9/2006 | Ross |
| 7,112,196 B2 | 9/2006 | Brosch et al. |
| 7,113,815 B2 | 9/2006 | O'Neil et al. |
| 7,122,005 B2 | 10/2006 | Shusterman |
| 7,123,950 B2 | 10/2006 | Mannheimer |
| 7,125,383 B2 | 10/2006 | Hoctor et al. |
| 7,127,278 B2 | 10/2006 | Melker et al. |
| 7,130,671 B2 | 10/2006 | Baker, Jr. et al. |
| 7,132,641 B2 | 11/2006 | Schulz et al. |
| 7,133,711 B2 | 11/2006 | Chernoguz et al. |
| 7,136,452 B2 | 11/2006 | Spartiotis et al. |
| 7,139,559 B2 | 11/2006 | Kenagy et al. |
| 7,142,901 B2 | 11/2006 | Kiani et al. |
| 7,143,305 B2 | 11/2006 | Hajji et al. |
| 7,158,822 B2 | 1/2007 | Payne, Jr. |
| 7,160,284 B2 | 1/2007 | Ullestad et al. |
| 7,161,484 B2 | 1/2007 | Tsoukalis |
| 7,162,288 B2 | 1/2007 | Nordstrom |
| 7,164,938 B2 | 1/2007 | Geddes et al. |
| 7,167,743 B2 | 1/2007 | Heruth et al. |
| 7,171,251 B2 | 1/2007 | Sarussi et al. |
| 7,179,228 B2 | 2/2007 | Banet |
| 7,181,264 B2 | 2/2007 | Wiesmann et al. |
| 7,181,505 B2 | 2/2007 | Haller et al. |
| 7,190,987 B2 | 3/2007 | Lindekugel |
| 7,192,403 B2 | 3/2007 | Russell et al. |
| 7,197,357 B2 | 3/2007 | Istvan et al. |
| 7,198,605 B2 | 4/2007 | Donofrio et al. |
| 7,198,778 B2 | 4/2007 | Mannheimer et al. |
| 7,209,775 B2 | 4/2007 | Bae et al. |
| 7,214,191 B2 | 5/2007 | Stringer et al. |
| 7,215,984 B2 | 5/2007 | Diab et al. |
| 7,218,232 B2 | 5/2007 | DiSilvestro et al. |
| 7,220,220 B2 | 5/2007 | Stubbs et al. |
| 7,222,624 B2 | 5/2007 | Rashad |
| 7,224,282 B2 | 5/2007 | Terauchi et al. |
| 7,225,006 B2 | 5/2007 | Al-Ali et al. |
| 7,225,007 B2 | 5/2007 | Al-Ali et al. |
| 7,229,400 B2 | 6/2007 | Elliott et al. |
| 7,236,811 B2 | 6/2007 | Schmitt |
| 7,245,953 B1 | 7/2007 | Parker |
| 7,248,905 B2 | 7/2007 | Fukuda et al. |
| 7,248,910 B2 | 7/2007 | Li et al. |
| 7,254,433 B2 | 8/2007 | Diab et al. |
| 7,254,434 B2 | 8/2007 | Schulz et al. |
| 7,254,444 B2 | 8/2007 | Moore et al. |
| 7,255,475 B2 | 8/2007 | Quinn et al. |
| 7,257,438 B2 | 8/2007 | Kinast |
| 7,257,448 B2 | 8/2007 | Crowe et al. |
| 7,263,393 B2 | 8/2007 | Smith et al. |
| 7,263,395 B2 | 8/2007 | Chan et al. |
| 7,270,636 B2 | 9/2007 | Lin et al. |
| 7,272,426 B2 | 9/2007 | Schmid |
| 7,280,858 B2 | 10/2007 | Al-Ali et al. |
| 7,289,837 B2 | 10/2007 | Mannheimer et al. |
| 7,295,866 B2 | 11/2007 | Al-Ali et al. |
| 7,297,119 B2 | 11/2007 | Westbrook et al. |
| 7,303,680 B2 | 12/2007 | Connell et al. |
| 7,305,262 B2 | 12/2007 | Brodnick et al. |
| 7,313,427 B2 | 12/2007 | Benni |
| 7,315,753 B2 | 1/2008 | Baker, Jr. et al. |
| 7,349,726 B2 | 3/2008 | Casciani et al. |
| 7,376,454 B2 | 5/2008 | Casciani et al. |
| 7,415,298 B2 | 8/2008 | Casciani et al. |
| 2001/0000790 A1 | 5/2001 | DeLonzor et al. |
| 2001/0009398 A1 | 7/2001 | Sekura et al. |
| 2001/0021803 A1 | 9/2001 | Blank et al. |
| 2001/0051767 A1 | 12/2001 | Williams et al. |
| 2002/0013538 A1 | 1/2002 | Teller |
| 2002/0026109 A1 | 2/2002 | Diab et al. |
| 2002/0028990 A1 | 3/2002 | Sheperd et al. |
| 2002/0038078 A1 | 3/2002 | Ito |
| 2002/0042558 A1 | 4/2002 | Mendelson |
| 2002/0052539 A1 | 5/2002 | Haller et al. |
| 2002/0068859 A1 | 6/2002 | Knopp |
| 2002/0084904 A1 | 7/2002 | De La Huerga |
| 2002/0091335 A1 | 7/2002 | John et al. |
| 2002/0095092 A1 | 7/2002 | Kondo et al. |
| 2002/0103445 A1 | 8/2002 | Rahdert et al. |
| 2002/0109600 A1 | 8/2002 | Mault et al. |
| 2002/0124295 A1 | 9/2002 | Fenwick et al. |
| 2002/0128544 A1 | 9/2002 | Diab et al. |
| 2002/0133067 A1 | 9/2002 | Jackson, III |
| 2002/0139368 A1 | 10/2002 | Bachinski |
| 2002/0148470 A1 | 10/2002 | Blue et al. |
| 2002/0151929 A1 | 10/2002 | Goto et al. |
| 2002/0156354 A1 | 10/2002 | Larson |
| 2002/0161309 A1 | 10/2002 | Marro |
| 2002/0173706 A1 | 11/2002 | Takatani et al. |
| 2002/0173708 A1 | 11/2002 | DeLonzor et al. |
| 2002/0173709 A1 | 11/2002 | Fine et al. |
| 2002/0190863 A1 | 12/2002 | Lynn |
| 2002/0198442 A1 | 12/2002 | Rantala et al. |
| 2003/0004547 A1 | 1/2003 | Owen et al. |
| 2003/0009119 A1 | 1/2003 | Kamm et al. |
| 2003/0009308 A1 | 1/2003 | Kirtley |
| 2003/0018243 A1 | 1/2003 | Gerhardt et al. |
| 2003/0023140 A1 | 1/2003 | Chance |
| 2003/0036685 A1 | 2/2003 | Goodman |
| 2003/0036690 A1 | 2/2003 | Geddes et al. |
| 2003/0045785 A1 | 3/2003 | Diab et al. |
| 2003/0065275 A1 | 4/2003 | Mault et al. |
| 2003/0073889 A1 | 4/2003 | Keilbach et al. |
| 2003/0073890 A1 | 4/2003 | Hanna |
| 2003/0086156 A1 | 5/2003 | McGuire |
| 2003/0100840 A1 | 5/2003 | Sugiura et al. |
| 2003/0120183 A1 | 6/2003 | Simmons |
| 2003/0122706 A1 | 7/2003 | Choi et al. |
| 2003/0125616 A1 | 7/2003 | Black et al. |
| 2003/0132495 A1 | 7/2003 | Mills et al. |
| 2003/0135099 A1 | 7/2003 | Al-Ali |
| 2003/0135127 A1 | 7/2003 | Sackner et al. |
| 2003/0144579 A1 | 7/2003 | Buss |
| 2003/0156288 A1 | 8/2003 | Barnum et al. |
| 2003/0162414 A1 | 8/2003 | Schulz et al. |
| 2003/0171662 A1 | 9/2003 | O'Connor et al. |
| 2003/0176776 A1 | 9/2003 | Huiku |
| 2003/0176810 A1 | 9/2003 | Maahs et al. |
| 2003/0181799 A1 | 9/2003 | Lindekugel et al. |
| 2003/0187337 A1 | 10/2003 | Tarassenko et al. |
| 2003/0189492 A1 | 10/2003 | Harvie |
| 2003/0195402 A1 | 10/2003 | Fein et al. |
| 2003/0197679 A1 | 10/2003 | Ali et al. |
| 2003/0212316 A1 | 11/2003 | Leiden et al. |
| 2003/0216728 A1 | 11/2003 | Stern et al. |
| 2003/0225323 A1 | 12/2003 | Kiani et al. |
| 2003/0225337 A1 | 12/2003 | Scharf et al. |
| 2003/0236452 A1 | 12/2003 | Melker et al. |
| 2003/0236647 A1 | 12/2003 | Yoon et al. |
| 2004/0002655 A1 | 1/2004 | Bolorforosh et al. |
| 2004/0006261 A1 | 1/2004 | Swedlow et al. |
| 2004/0007585 A1 | 1/2004 | Griffith et al. |
| 2004/0010188 A1 | 1/2004 | Wasserman et al. |
| 2004/0024297 A1 | 2/2004 | Chen et al. |
| 2004/0024326 A1 | 2/2004 | Yeo et al. |
| 2004/0030258 A1 | 2/2004 | Williams et al. |
| 2004/0034293 A1 | 2/2004 | Kimball |
| 2004/0039272 A1 | 2/2004 | Abdul-Hafiz et al. |
| 2004/0039273 A1 | 2/2004 | Terry |
| 2004/0044545 A1 | 3/2004 | Wiesmann et al. |
| 2004/0054269 A1 | 3/2004 | Rantala et al. |
| 2004/0054287 A1 | 3/2004 | Stephens |
| 2004/0054291 A1 | 3/2004 | Schulz et al. |
| 2004/0059209 A1 | 3/2004 | Al-Ali et al. |
| 2004/0059210 A1 | 3/2004 | Stetson |
| 2004/0064020 A1 | 4/2004 | Diab et al. |

| | | | | | |
|---|---|---|---|---|---|
| 2004/0064097 A1 | 4/2004 | Peterson | 2005/0043599 A1 | 2/2005 | O'Mara |
| 2004/0064165 A1 | 4/2004 | Thompson | 2005/0043600 A1 | 2/2005 | Diab et al. |
| 2004/0068164 A1 | 4/2004 | Diab et al. | 2005/0043763 A1 | 2/2005 | Marcovecchio et al. |
| 2004/0082842 A1 | 4/2004 | Lumba et al. | 2005/0049465 A1 | 3/2005 | Wang |
| 2004/0087846 A1 | 5/2004 | Wasserman | 2005/0049470 A1 | 3/2005 | Terry |
| 2004/0092805 A1 | 5/2004 | Yarita | 2005/0049471 A1 | 3/2005 | Aceti |
| 2004/0092919 A1 | 5/2004 | Ritchie et al. | 2005/0049501 A1 | 3/2005 | Conero et al. |
| 2004/0097797 A1 | 5/2004 | Porges et al. | 2005/0059869 A1 | 3/2005 | Scharf et al. |
| 2004/0098009 A1 | 5/2004 | Boecker et al. | 2005/0070776 A1 | 3/2005 | Mannheimer et al. |
| 2004/0100784 A1 | 5/2004 | Willers et al. | 2005/0070778 A1 | 3/2005 | Lakcey et al. |
| 2004/0102931 A1 | 5/2004 | Ellis et al. | 2005/0075550 A1 | 4/2005 | Lindekugel |
| 2004/0107065 A1 | 6/2004 | Al-Ali et al. | 2005/0080345 A1 | 4/2005 | Finburgh et al. |
| 2004/0116788 A1 | 6/2004 | Chernoguz et al. | 2005/0085799 A1 | 4/2005 | Luria et al. |
| 2004/0116789 A1 | 6/2004 | Boaz et al. | 2005/0090754 A1 | 4/2005 | Wolff et al. |
| 2004/0117891 A1 | 6/2004 | Hannula et al. | 2005/0096557 A1 | 5/2005 | Vosburgh et al. |
| 2004/0122300 A1 | 6/2004 | Boas et al. | 2005/0101845 A1 | 5/2005 | Nihtila |
| 2004/0122302 A1 | 6/2004 | Mason et al. | 2005/0102167 A1 | 5/2005 | Kapoor |
| 2004/0133087 A1 | 7/2004 | Ali et al. | 2005/0113650 A1 | 5/2005 | Pacione et al. |
| 2004/0133088 A1 | 7/2004 | Al-Ali et al. | 2005/0113656 A1 | 5/2005 | Chance |
| 2004/0138538 A1 | 7/2004 | Stetson | 2005/0113703 A1 | 5/2005 | Farringdon et al. |
| 2004/0138540 A1 | 7/2004 | Baker, Jr. et al. | 2005/0114154 A1 | 5/2005 | Wolkoweiz et al. |
| 2004/0143172 A1 | 7/2004 | Fudge et al. | 2005/0171576 A1 | 8/2005 | Williams et al. |
| 2004/0144391 A1 | 7/2004 | Brady et al. | 2005/0177034 A1 | 8/2005 | Beaumont |
| 2004/0147821 A1 | 7/2004 | Al-Ali et al. | 2005/0182458 A1 | 8/2005 | Goedeke |
| 2004/0147822 A1 | 7/2004 | Al-Ali et al. | 2005/0188991 A1 | 9/2005 | Sun et al. |
| 2004/0147823 A1 | 7/2004 | Kiani et al. | 2005/0190068 A1 | 9/2005 | Gentry et al. |
| 2004/0147824 A1 | 7/2004 | Diab et al. | 2005/0197548 A1 | 9/2005 | Dietiker |
| 2004/0147974 A1 | 7/2004 | Engmark et al. | 2005/0206518 A1 | 9/2005 | Welch et al. |
| 2004/0149282 A1 | 8/2004 | Hickle | 2005/0215847 A1 | 9/2005 | Heruth et al. |
| 2004/0152965 A1 | 8/2004 | Diab et al. | 2005/0215880 A1 | 9/2005 | Harrison et al. |
| 2004/0158134 A1 | 8/2004 | Diab et al. | 2005/0215947 A1 | 9/2005 | Heruth et al. |
| 2004/0158135 A1 | 8/2004 | Baker, Jr. et al. | 2005/0216064 A1 | 9/2005 | Heruth et al. |
| 2004/0162472 A1 | 8/2004 | Berson et al. | 2005/0216199 A1 | 9/2005 | Banet |
| 2004/0163648 A1 | 8/2004 | Burton | 2005/0222522 A1 | 10/2005 | Heruth et al. |
| 2004/0171920 A1 | 9/2004 | Mannheimer et al. | 2005/0228234 A1 | 10/2005 | Yang |
| 2004/0171948 A1 | 9/2004 | Terry | 2005/0228248 A1 | 10/2005 | Dietiker |
| 2004/0173456 A1 | 9/2004 | Boos et al. | 2005/0228297 A1 | 10/2005 | Banet et al. |
| 2004/0176671 A1 | 9/2004 | Fine et al. | 2005/0228299 A1 | 10/2005 | Banet |
| 2004/0181133 A1 | 9/2004 | Al-Ali et al. | 2005/0231686 A1 | 10/2005 | Rathjen |
| 2004/0181134 A1 | 9/2004 | Baker, Jr. et al. | 2005/0234312 A1 | 10/2005 | Suzuki et al. |
| 2004/0186358 A1 | 9/2004 | Chernow et al. | 2005/0234317 A1 | 10/2005 | Kiani |
| 2004/0199063 A1 | 10/2004 | O'Neil et al. | 2005/0234518 A1 | 10/2005 | Heruth et al. |
| 2004/0204636 A1 | 10/2004 | Diab et al. | 2005/0240087 A1 | 10/2005 | Keenan et al. |
| 2004/0204637 A1 | 10/2004 | Diab et al. | 2005/0256523 A1 | 11/2005 | Chen et al. |
| 2004/0204638 A1 | 10/2004 | Diab et al. | 2005/0261594 A1 | 11/2005 | Banet |
| 2004/0204639 A1 | 10/2004 | Casciani et al. | 2005/0268916 A1 | 12/2005 | Mumford et al. |
| 2004/0204865 A1 | 10/2004 | Lee et al. | 2005/0277819 A1 | 12/2005 | Kiani et al. |
| 2004/0210146 A1 | 10/2004 | Diab et al. | 2005/0283059 A1 | 12/2005 | Iyer et al. |
| 2004/0215069 A1 | 10/2004 | Mannheimer | 2005/0283082 A1 | 12/2005 | Geddes et al. |
| 2004/0221370 A1 | 11/2004 | Hannula et al. | 2006/0009685 A1 | 1/2006 | Finarov et al. |
| 2004/0230107 A1 | 11/2004 | Asada et al. | 2006/0009698 A1 | 1/2006 | Banet et al. |
| 2004/0230108 A1 | 11/2004 | Melker et al. | 2006/0020181 A1 | 1/2006 | Schmidt |
| 2004/0230116 A1 | 11/2004 | Cowan et al. | 2006/0030049 A1 | 2/2006 | Bhimani et al. |
| 2004/0231772 A1 | 11/2004 | Leonard et al. | 2006/0030767 A1 | 2/2006 | Lang et al. |
| 2004/0236196 A1 | 11/2004 | Diab et al. | 2006/0036179 A1 | 2/2006 | Miller |
| 2004/0236207 A1 | 11/2004 | Widener et al. | 2006/0047447 A1 | 3/2006 | Brady et al. |
| 2004/0236242 A1 | 11/2004 | Graham et al. | 2006/0058593 A1 | 3/2006 | Drinan et al. |
| 2004/0242980 A1 | 12/2004 | Kiani et al. | 2006/0058594 A1 | 3/2006 | Ishizuka et al. |
| 2004/0242981 A1 | 12/2004 | Pattisapu | 2006/0058690 A1 | 3/2006 | Bartnik et al. |
| 2004/0249252 A1 | 12/2004 | Fine et al. | 2006/0064024 A1 | 3/2006 | Schnall |
| 2004/0254490 A1 | 12/2004 | Egli | 2006/0064133 A1 | 3/2006 | Von Arx et al. |
| 2004/0254501 A1 | 12/2004 | Mault | 2006/0064134 A1 | 3/2006 | Mazar et al. |
| 2004/0257557 A1 | 12/2004 | Block et al. | 2006/0064142 A1 | 3/2006 | Chavan et al. |
| 2004/0260161 A1 | 12/2004 | Melker et al. | 2006/0064143 A1 | 3/2006 | Von Arx et al. |
| 2004/0267103 A1 | 12/2004 | Li et al. | 2006/0074283 A1 | 4/2006 | Henderson et al. |
| 2004/0267104 A1 | 12/2004 | Hannula et al. | 2006/0074324 A1 | 4/2006 | Wu et al. |
| 2004/0267140 A1 | 12/2004 | Ito et al. | 2006/0084848 A1 | 4/2006 | Mitchnick |
| 2004/0267145 A1 | 12/2004 | David et al. | 2006/0084852 A1 | 4/2006 | Mason et al. |
| 2005/0001728 A1 | 1/2005 | Appelt et al. | 2006/0085227 A1 | 4/2006 | Rosenfeld et al. |
| 2005/0004479 A1 | 1/2005 | Townsend et al. | 2006/0089547 A1 | 4/2006 | Sarussi |
| 2005/0010092 A1 | 1/2005 | Weber et al. | 2006/0095032 A1 | 5/2006 | Jackson et al. |
| 2005/0020887 A1 | 1/2005 | Goldberg | 2006/0100496 A1 | 5/2006 | Avron |
| 2005/0020894 A1 | 1/2005 | Norris et al. | 2006/0100530 A1 | 5/2006 | Kliot et al. |
| 2005/0020919 A1 | 1/2005 | Stringer et al. | 2006/0100618 A1 | 5/2006 | Chan et al. |
| 2005/0027207 A1 | 2/2005 | Westbrook et al. | 2006/0106294 A1 | 5/2006 | Maser et al. |
| 2005/0029432 A1 | 2/2005 | Bacarella et al. | 2006/0122517 A1 | 6/2006 | Banet et al. |
| 2005/0033128 A1 | 2/2005 | Ali et al. | 2006/0122520 A1 | 6/2006 | Banet et al. |
| 2005/0033129 A1 | 2/2005 | Edgar, Jr. et al. | 2006/0124128 A1 | 6/2006 | Deane et al. |
| 2005/0041531 A1 | 2/2005 | Sekura et al. | 2006/0125623 A1 | 6/2006 | Applet et al. |

| | | |
|---|---|---|
| 2006/0132382 A1 | 6/2006 | Jannard |
| 2006/0133362 A1 | 6/2006 | Stein et al. |
| 2006/0142640 A1 | 6/2006 | Takahashi |
| 2006/0149132 A1 | 7/2006 | Iddan |
| 2006/0149339 A1 | 7/2006 | Burnes et al. |
| 2006/0167351 A1 | 7/2006 | Isaacson et al. |
| 2006/0173247 A1 | 8/2006 | Medina |
| 2006/0183980 A1 | 8/2006 | Yang |
| 2006/0184051 A1 | 8/2006 | Hempstead et al. |
| 2006/0189859 A1 | 8/2006 | Kiani et al. |
| 2006/0195026 A1 | 8/2006 | Casciani et al. |
| 2006/0195027 A1 | 8/2006 | Casciani et al. |
| 2006/0195028 A1 | 8/2006 | Hannula et al. |
| 2006/0211929 A1 | 9/2006 | Casciani et al. |
| 2006/0211942 A1 | 9/2006 | Hoctor et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224040 A1 | 10/2006 | Khait et al. |
| 2006/0224058 A1 | 10/2006 | Mannheimer |
| 2006/0224326 A1 | 10/2006 | St. Ores et al. |
| 2006/0224421 A1 | 10/2006 | St. Ores et al. |
| 2006/0229510 A1 | 10/2006 | Fein et al. |
| 2006/0229511 A1 | 10/2006 | Fein et al. |
| 2006/0241358 A1 | 10/2006 | Al-Ali et al. |
| 2006/0241384 A1 | 10/2006 | Fisher et al. |
| 2006/0241510 A1 | 10/2006 | Halperin et al. |
| 2006/0247501 A1 | 11/2006 | Ali |
| 2006/0247504 A1 | 11/2006 | Tice |
| 2006/0253010 A1 | 11/2006 | Brady et al. |
| 2006/0253953 A1 | 11/2006 | Williams |
| 2006/0258921 A1 | 11/2006 | Addison et al. |
| 2006/0258922 A1 | 11/2006 | Mason et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1 | 11/2006 | Hannula et al. |
| 2006/0264726 A1 | 11/2006 | Mannheimer et al. |
| 2006/0264727 A1 | 11/2006 | Mannheimer et al. |
| 2006/0264771 A1 | 11/2006 | Lin et al. |
| 2006/0276700 A1 | 12/2006 | O'Neil et al. |
| 2006/0276701 A1 | 12/2006 | Ray |
| 2006/0281984 A1 | 12/2006 | Mannheimer et al. |
| 2007/0032712 A1 | 2/2007 | Raridan et al. |
| 2007/0032715 A1 | 2/2007 | Eghbal et al. |
| 2007/0032732 A1 | 2/2007 | Shelley et al. |
| 2007/0060808 A1 | 3/2007 | Hoarau |
| 2007/0073117 A1 | 3/2007 | Raridan |
| 2007/0073121 A1 | 3/2007 | Hoarau et al. |
| 2007/0073123 A1 | 3/2007 | Raridan |
| 2007/0073126 A1 | 3/2007 | Raridan, Jr. |
| 2007/0078316 A1 | 4/2007 | Hoarau et al. |
| 2007/0100218 A1 | 5/2007 | Sweitzer et al. |
| 2007/0100219 A1 | 5/2007 | Sweitzer et al. |
| 2007/0142715 A1 | 6/2007 | Banet et al. |
| 2007/0149871 A1 | 6/2007 | Sarussi et al. |
| 2007/0208269 A1 | 9/2007 | Mumford et al. |
| 2007/0260129 A1 | 11/2007 | Chin |
| 2007/0293746 A1 | 12/2007 | Sarussi et al. |
| 2008/0009691 A1 | 1/2008 | Parker |
| 2008/0076988 A1 | 3/2008 | Sarussi et al. |
| 2008/0076990 A1 | 3/2008 | Sarussi et al. |
| 2008/0081967 A1 | 4/2008 | Andersohn et al. |
| 2008/0083412 A1* | 4/2008 | Henry et al. ............. 128/207.11 |
| 2008/0139908 A1 | 6/2008 | Kurth |
| 2008/0143080 A1 | 6/2008 | Burr |
| 2008/0146890 A1 | 6/2008 | LeBoeuf et al. |
| 2008/0165017 A1 | 7/2008 | Schwartz |
| 2008/0177163 A1 | 7/2008 | Wang et al. |
| 2008/0221413 A1 | 9/2008 | Hoarau |
| 2008/0221414 A1 | 9/2008 | Baker |
| 2008/0228053 A1 | 9/2008 | Wang et al. |
| 2008/0230363 A1 | 9/2008 | Yang et al. |
| 2008/0316488 A1 | 12/2008 | Mao et al. |
| 2009/0163787 A1* | 6/2009 | Mannheimer et al. ........ 600/324 |

FOREIGN PATENT DOCUMENTS

| | | |
|---|---|---|
| DE | 19632361 | 2/1997 |
| EP | 0127947 | 12/1984 |
| EP | 0204259 | 12/1986 |
| EP | 0724860 | 8/1996 |
| FR | 2685865 | 1/1992 |
| JP | 2111343 | 4/1990 |
| JP | 5049625 | 3/1993 |
| JP | 6014906 | 1/1994 |
| JP | 6269430 | 9/1994 |
| JP | 7001273 | 1/1995 |
| JP | 7236625 | 9/1995 |
| JP | 2000237170 | 9/2000 |
| JP | 3116259 | 10/2000 |
| JP | 3116260 | 10/2000 |
| JP | 24148069 | 10/2002 |
| JP | 25095465 A2 | 9/2003 |
| JP | 2003275192 | 9/2003 |
| JP | 2004089546 | 3/2004 |
| JP | 26122458 A2 | 10/2004 |
| JP | 2004329406 | 11/2004 |
| JP | 2004337605 | 12/2004 |
| JP | 2004344367 | 12/2004 |
| JP | 2004351107 | 12/2004 |
| JP | 26201114 A2 | 1/2005 |
| JP | 26239267 A2 | 3/2005 |
| JP | 26326153 A2 | 5/2005 |
| JP | 26297125 A2 | 6/2006 |
| JP | 28119288 A2 | 11/2006 |
| JP | 28161657 A2 | 12/2006 |
| WO | WO8909566 | 10/1989 |
| WO | 9001293 A1 | 2/1990 |
| WO | WO9001293 | 2/1990 |
| WO | 9111137 A1 | 8/1991 |
| WO | WO9111137 | 8/1991 |
| WO | WO98/57577 | 12/1993 |
| WO | WO9502358 | 1/1995 |
| WO | 9512349 A1 | 5/1995 |
| WO | WO9736536 | 10/1997 |
| WO | 9817174 A1 | 4/1998 |
| WO | 9947039 A1 | 9/1999 |
| WO | WO9947039 | 9/1999 |
| WO | WO0059374 | 10/2000 |
| WO | 0176471 A1 | 10/2001 |
| WO | WO03009750 | 2/2003 |
| WO | WO2005010567 | 2/2005 |
| WO | WO2005010568 | 2/2005 |
| WO | 2007048039 A2 | 4/2007 |
| WO | 2008085511 A1 | 9/2009 |

OTHER PUBLICATIONS

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Gosney, S., et al.; "An alternative position for the pulse oximeter probe," *Anaesthesia*, vol. 56, p. 493 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investigation of oesophageal photoplethysmographic signals and blood oxygen saturation measurements in cardiothoracic surgery patients," *Physiological Measurement*, vol. 23, No. 3, pp. 533-545 (Aug. 2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Avidan, A.; "Pulse oximeter ear probe," *Anaesthesia*, vol. 58, pp. 726 (2003).

Matsui, A., et al.; "Pulse Oximeter," *Neonatal Care*, vol. 16, No. 3, pp. 38-45 (2003) (Article in Japanese—contains English summary of article).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

"Smaller Product, Tighter Tolerances Pose Dispensing Challenges for Medical Device Manufacturer," *Adhesives Age*, pp. 40-41 (Oct. 1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1919, posted date: Aug. 6, 2002.

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

Ferrell, T.L., et al.; "Medical Telesensors," *SPIE*, vol. 3253, pp. 193-198 (1998).

Rohling, Roman, et al.; "Clinical Investigation of a New Combined Pulse Oximetry and Carbon Dioxide Tension Sensor in Adult Anaesthesia," *Journal of Clinical Monitoring and Computing*, vol. 15; pp. 23-27 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.

Schulz, Christian Eric; "Design of a Pulse Oximetry Sensor Housing Assembly," California State University Master's Thesis, *UMI Dissertation Services*, UMI No. 1401306, (May 2000) 63 pages.

Wendelken, Suzanne, et al.; "The Feasibility of Using a Forehead Reflectance Pulse Oximeter for Automated Remote Triage," *IEEE*, pp. 180-181 (2004).

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Kocher, Serge, et al.; "Performance of a Digital $PCO_2/SPO_2$ Ear Sensor," *Journal of Clinical Monitoring and Computing*, vol. 18, pp. 75-59 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Urquhart, C., et al.; "Ear probe pulse oximeters and neonates," *Anaesthesia*, vol. 60, p. 294 (2005).

Bentley, David J. et al.; "Measure Pressure with Thin Film"; Paper Film & Foil Converter; May 1, 2003.

http://www.fcw.com.my/fujifilm.html, date: 2006.

* cited by examiner

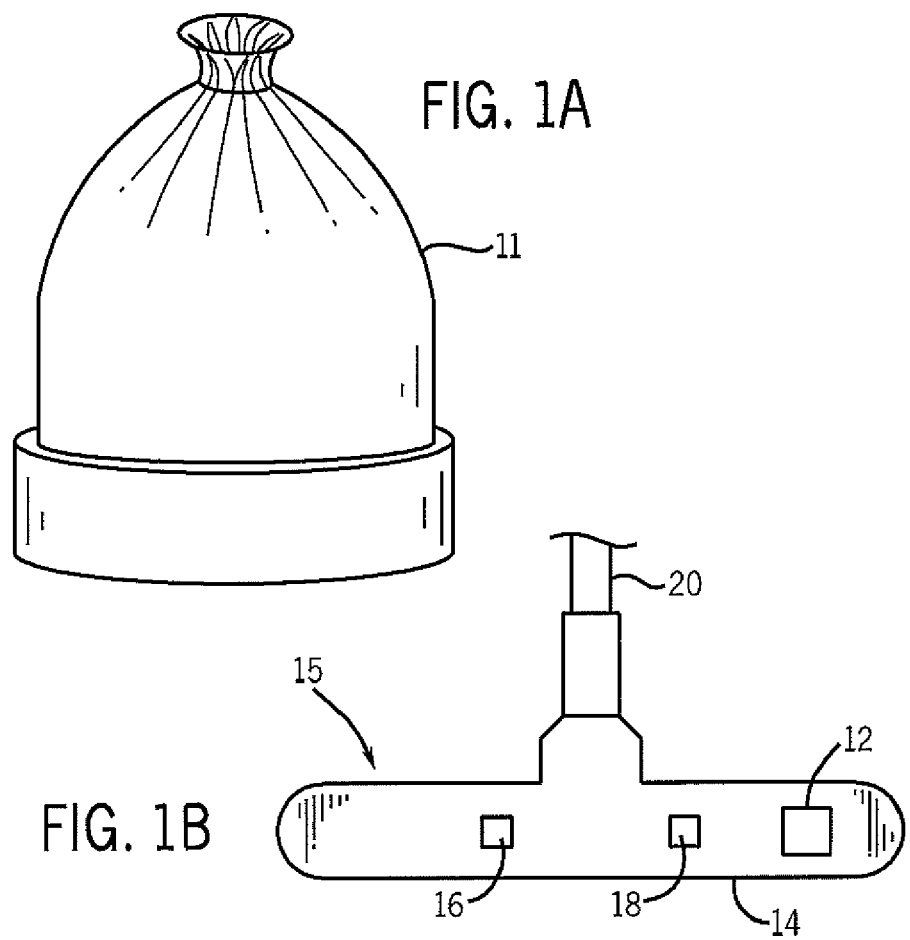
FIG. 1A
FIG. 1B
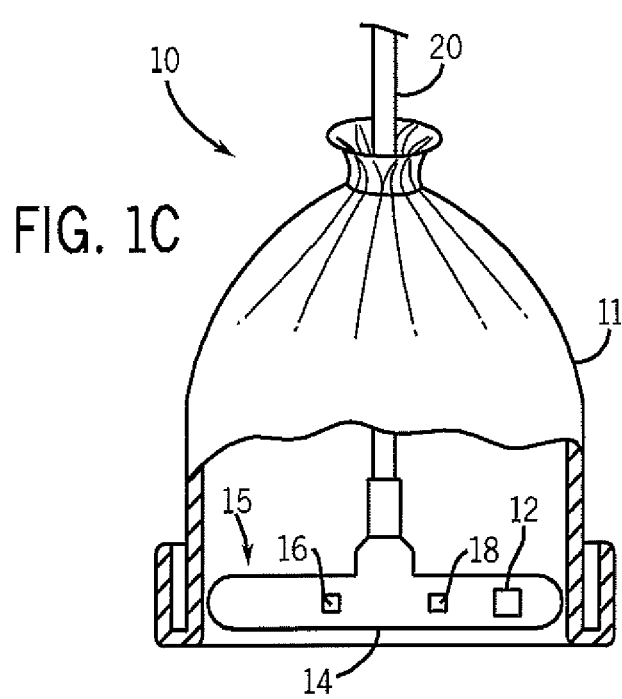
FIG. 1C

MEDICAL SENSOR AND TECHNIQUE FOR USING THE SAME

BACKGROUND

The present disclosure relates generally to medical devices and, more particularly, to sensors used for sensing physiological parameters of a patient.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry measurement often involves placement of a sensor on a patient's tissue, typically via a lightly adhesive sensor, a clip-style sensor, or a sensor that may be fitted through pressure contact with the tissue. Because these sensors are worn for up to four hours before the sensor is repositioned, pulse oximetry sensors may slightly deform the underlying tissue if the pressure contact is too great. Deformed tissue may be associated with motion artifacts in cases where pressure from the sensor alters the blood flow into the tissue, leading to changes in the pulse oximetry readings.

BRIEF DESCRIPTION OF THE DRAWINGS

Advantages of the disclosure may become apparent upon reading the following detailed description and upon reference to the drawings in which:

FIG. 1A illustrates a perspective view of an exemplary hat structure for holding a pulse oximetry sensor on a patient's tissue;

FIG. 1B illustrates a perspective view of an exemplary pulse oximetry sensor body with an integrated pressure sensor that may be incorporated with the hat of FIG. 1A;

FIG. 1C illustrates a perspective view of the hat of FIG. 1A with the pulse oximetry sensor with an integrated pressure sensor of FIG. 1B;

DETAILED DESCRIPTION

Figure 2A:
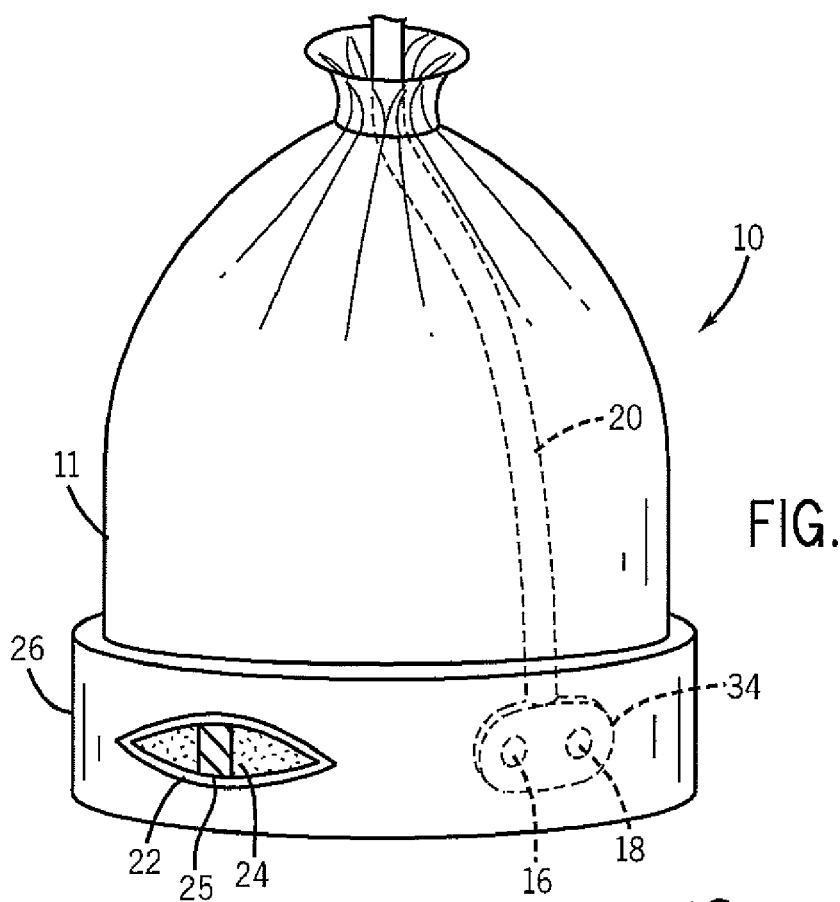
FIG. 2A illustrates a perspective view of an exemplary hat pulse oximetry sensor with a pressure-sensitive film sensor incorporated into the band of the hat.

One or more embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with embodiments, sensors for pulse oximetry or other applications utilizing spectrophotometry are provided that apply a sensor to a tissue such that the pressure is sufficient to obtain sensor readings but not so great as to cause patient discomfort or signal artifacts associated with tissue deformation. For example, sensors are provided that include force-sensitive devices adapted to assess the pressure experienced of the sensor against a patient's tissue while in use. Further, sensor assemblies as provided herein may be adapted to alter the pressure that is exerted on a patient's tissue.

In an embodiment, an oximetry sensor with an integral pressure transducer may be adapted for placement in a hat (for example, a neonatal stocking cap), a headband, or other wearable structure (i.e. a glove, a sock, a wristband) to apply the sensor on the body of the user, FIGS. 1A-1C illustrate an assembly drawing of an embodiment of a sensor assembly 10 including a wearable structure, which may be a hat 11, as shown in FIG. 1A. A reflectance-type pulse oximetry sensor 15, as shown in FIG. 1B, is adapted to be placed or adhered to the inside of a hat 11.

In an embodiment, the sensor 15 includes a substrate 14 that may be made from any suitable material. In an embodiment, the substrate 14 is a foam or other conformable material. In one embodiment, the substrate 14 is black or dark in color to absorb stray light and minimize any shunting of light between sensor and patient skin. In one embodiment, the substrate 14 may include an adhesive material to secure the sensor directly to the tissue. In one embodiment, the sensor 15 may include an emitter 16 containing emitters for two or more wavelengths of light and a detector 18 spaced apart from the emitter 16. The sensor 15 also includes a pressure transducer 12. The pressure transducer 12 is adapted to provide an indication of the pressure of the sensor 15 against the tissue.

Also shown in FIG. 1B is a cable 20 for providing drive current to the pressure transducer 12, providing the pressure signal to a downstream medical device, providing drive current to the LED, and providing the detector signal to the medical device, according to an embodiment. In addition to providing the electrical connection to the downstream medical device, the cable may provide shielding to protect the small signals from the detector against external electrical interference. In addition, the sensor 15 may include suitable structures for providing electrical connections to the cable and/or downstream medical device, such as a flex circuit, a Faraday shield, and leads connecting the optical components and the pressure transducer of the sensor 15 to the electrical components.

In an embodiment, the sensor assembly 10 is shown fully assembled in FIG. 1C. As shown, the sensor 15 is positioned on the interior of the hat 11 such that the emitter 16 and detector 18, as well as the pressure transducer 12, may come into contact with the skin when the sensor assembly 10 is applied to a patient. The sensor 15 may be attached (e.g., adhered or sewn into) to the inside band of a hat. In one embodiment, the hat may include indicators to position the sensor 15 on a particular location on the patient's forehead, for example to position the sensor 15 on the lower forehead region, above the eyebrow, with the sensor optics (emitter 16 and detector 18) located above and predominantly lateral to or centered over the iris. The location of the reflectance sensor 15 in the hat allows appropriate placement of the sensor in the desired forehead location by a user not skilled in sensor placement. FIG. 1C shows that the cable 20 is positioned through a hole in the top of the hat 11. In an embodiment, the cable 20 may be adhered or otherwise constrained in the hat 11 so that the cable generally is positioned away from the sensor 15 to avoid interfering with the patient's eyesight or bothering the patient.

In some embodiments, it is envisioned that force or pressure data generated from the force-sensitive structures may be further processed by a downstream monitor to generate displays or other information related to the pressure exerted on the tissue by the sensor assembly 10. However, as patients may not be familiar with the medical monitor icons and displays that may be used in conjunction with a sensor assembly 10, in certain embodiments it may be advantageous to provide a sensor assembly 10 with a pressure-sensitive signal that is easily identifiable. FIG. 2A illustrates a sensor assembly 10 that may be applied to a patient's head. The sensor assembly 10 includes a hat 11 and a pulse oximetry sensor 34, including an emitter 16, a detector 18, and a cable 20. The pulse oximetry sensor 34 is placed on the interior of the hat band 26. The sensor assembly 10 also includes a pressure-sensitive film 24 that is adapted to change color upon the application of force. The pressure-sensitive film 24 may be viewed through a viewing window, depicted here as a buttonhole 22 formed in the knit fabric of the hat 11.

Figure 2B:
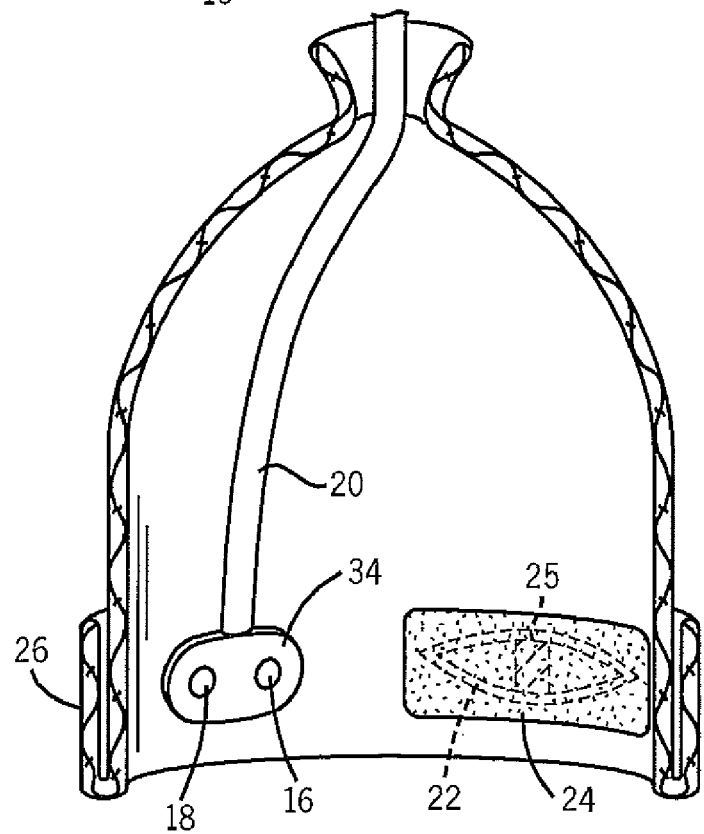
FIG. 2B is a cross-sectional view of the exemplary hat pulse oximetry sensor of FIG. 2A.

As shown in FIG. 2B, the pressure-sensitive film 24 may be located on the interior of the hat band 26 at approximately the same latitude as the pulse oximetry sensor 34. Such placement may allow the pressure indication of the pressure-sensitive film 24 to approximate the force exerted by the pulse oximetry sensor 34 on the tissue, assuming that the hat band 26 applies force equally around the head. In an embodiment, the pressure-sensitive film 24 may turn from colorless to red as pressure is increased against the tissue. In one embodiment, the pressure-sensitive film 24 may be Pressurex® film, available from Sensor Products Inc. (East Hanover, N.J.), which increases in red color intensity in relation to the amount of force applied. In one embodiment, the sensor assembly 10 may also include a reference color strip 25 that may be compared to the color in the pressure-sensitive film 24. When the color matches or is brighter than the color in the reference color strip 25, a patient or caregiver may adjust the sensor assembly 10 so that less pressure is exerted on the tissue or may choose a hat of a larger size to fit the patient.

Figure 3:
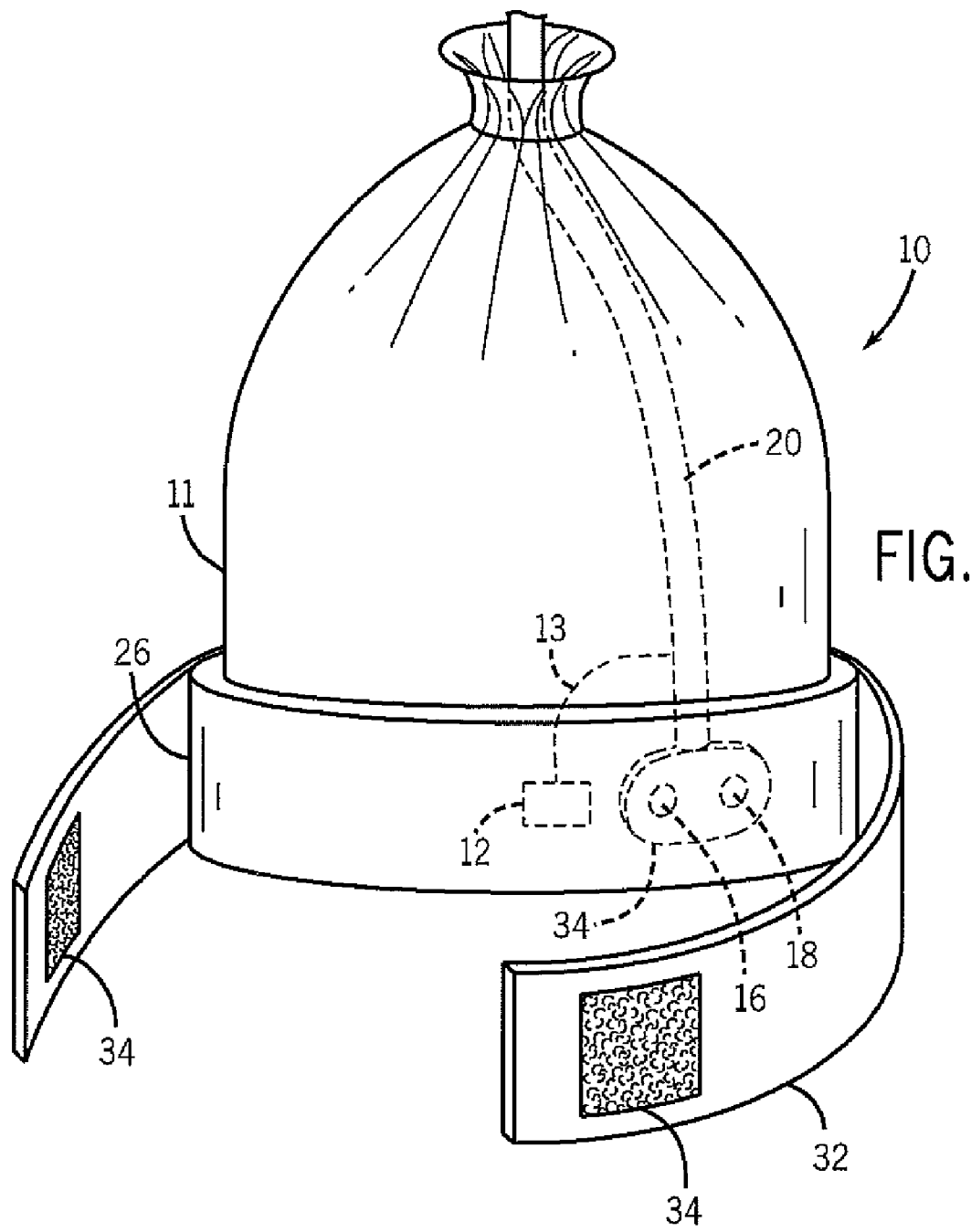
FIG. 3 illustrates an exemplary hat pulse oximetry sensor with a tightening structure.

FIG. 3 shows an embodiment of a hat-based sensor assembly 10 for pulse oximetry or other medical monitoring that includes a tightening device, shown here as a strap 32. In certain instances, a patient's head size may fall in between hat sizes. In such cases, it may be preferable to apply a slightly too large hat to the patient to avoid placing a hat on the patient that will be uncomfortably tight. However, if the hat is too large, the emitter 16 and the detector 18 of the sensor 34 may not come into sufficient contact with the forehead tissue for accurate sensor readings. To overcome this problem, a caregiver may tighten the hat-based sensor assembly 10 with a tightening strap 32. The strap may be circled over the band of the hat 11 to tighten the position of the sensor 34 on the skin. The strap 32 may be closed at the appropriate tightness by any suitable means, such as a hook and loop closure 34 depicted here. In certain embodiments, the tightness may be monitored by a pressure transducer 12 connected to a cable 20 by a lead 13. The pressure transducer 12 may provide feedback relating to the tightness of the hat 11 on the tissue. If the hat is too tight or too loose, a signal may be carried by the cable 20 to a downstream monitor, which may display an appropriate warning or indication.

Figure 4:
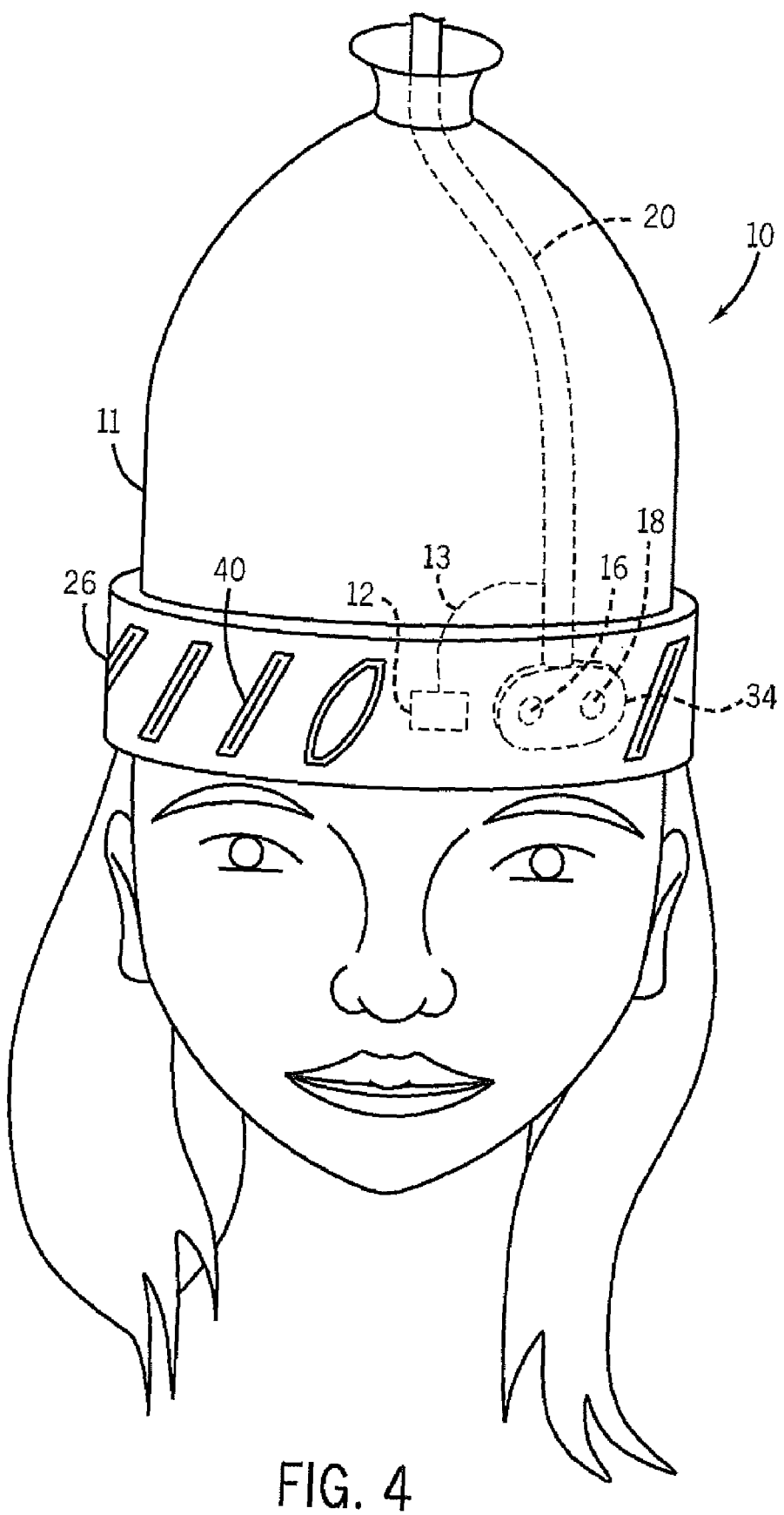
FIG. 4 illustrates an exemplary hat pulse oximetry sensor with indicators for slit-shaped openings in the hat to change the applied pressure to the tissue.
Figure 5:
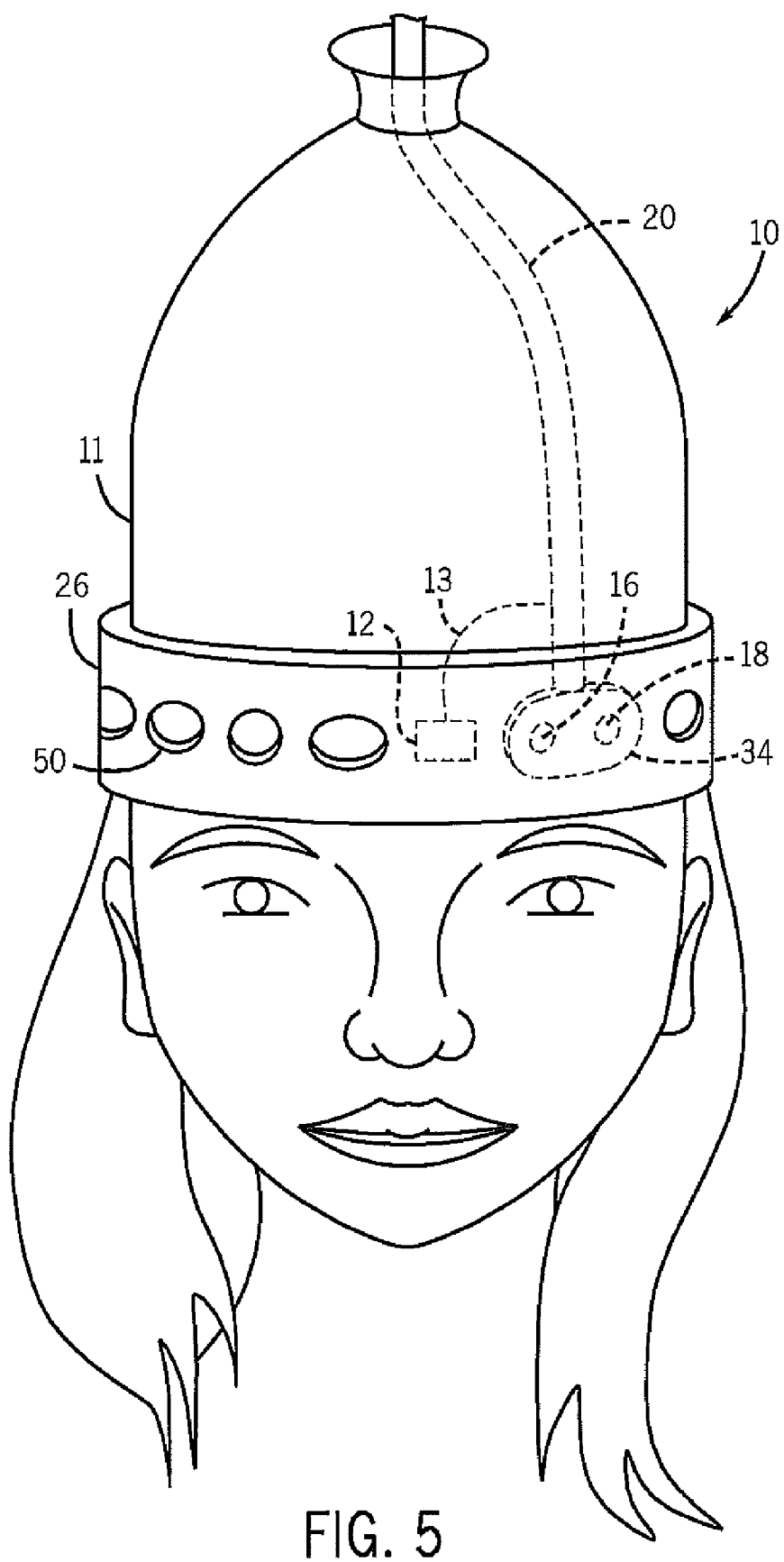
FIG. 5 illustrates an exemplary hat pulse oximetry sensor with indicators for holes that may be punched in the hat to change the applied pressure to the tissue.

In an embodiment, the tightness of a hat or headband-based sensor assembly may be adjusted by creating openings in the structure of the hat or headband. FIG. 4 shows a hat-based sensor assembly 10 that includes a sensor 34. The hat includes indicia for slits 40 that may be cut in the fabric of the hat to reduce the tension applied by the hat band 26. If a pressure transducer 12 provides a signal that the hat is too tight, the hat may be adjusted by taking it off the head of the patient and cutting the fabric where indicated by the slits 40. Each slit 40 may be cut one at a time, each time returning the hat to the head of the patient to check the tightness after cutting. In this manner, the hat may have multiple levels of adjustability. For example, a hat that is very tight may be very comfortable after cutting several slits 40, while a hat that is only mildly tight may be rendered comfortable by cutting only one slit 40. In other embodiments, the indicia may indicate other suitable shapes that may be easily cut into the band of the hat. Shown in FIG. 5 is a hat-based sensor assembly 10 that includes indicia for holes 50 that may be punched into the fabric of the hat to reduce the tension applied by the hat band 26. Such an embodiment may be advantageous for settings in which scissors are not readily available and/or desirable. In one embodiment the hat-based sensor assembly 10 may be sold as a kit with a hole-punch that is adapted to punch a hole that matches the size of the hole-shaped indicia 50.

Figure 6A:
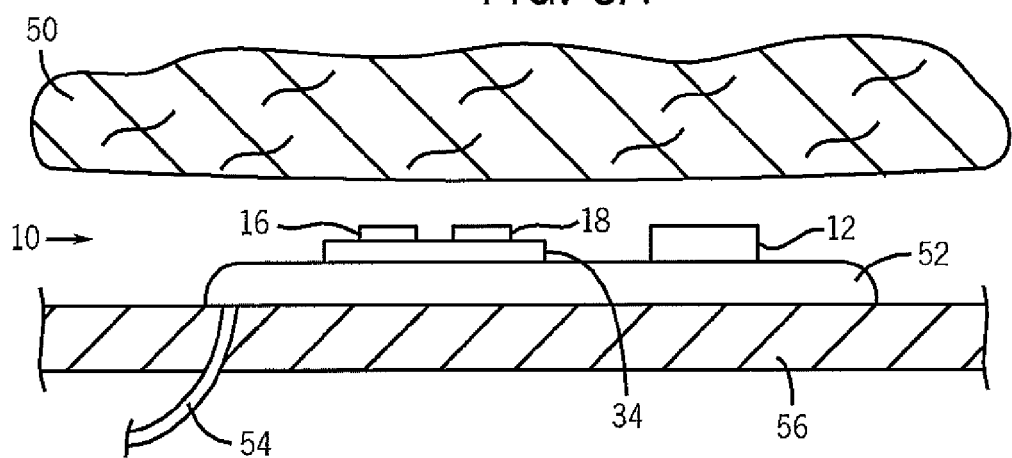
FIG. 6A illustrates a cross-sectional view of an exemplary headband-style sensor with a pressure balloon adapted to apply a pulse oximetry sensor and a pressure sensor against a patient's tissue.
Figure 6B:
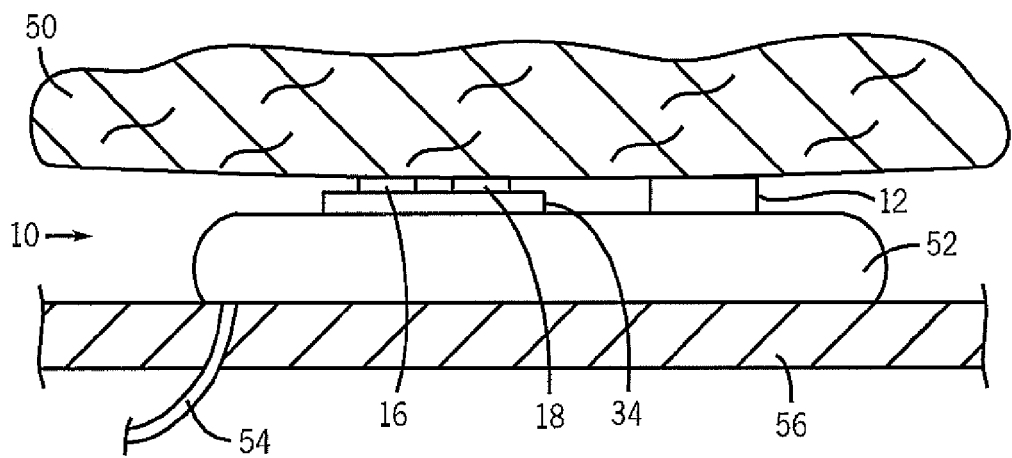
FIG. 6B illustrates a cross-sectional view of the sensor of FIG. 6A in which the balloon has been inflated to apply the pulse oximetry sensor and pressure sensor to the tissue.
Figure 7:
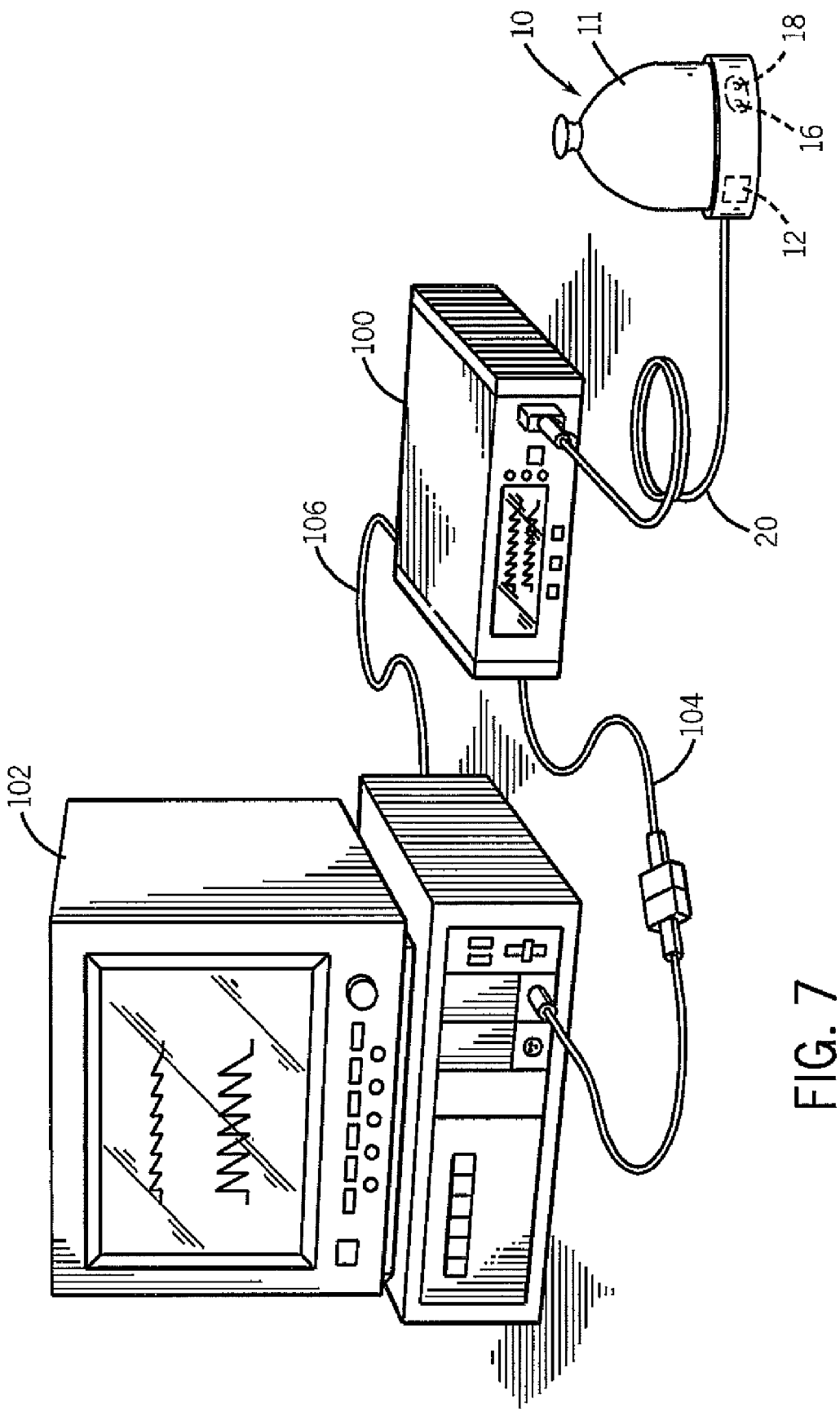
FIG. 7 illustrates an exemplary pulse oximetry system coupled to a multi-parameter patient monitor and a sensor.

FIGS. 6A and 6B illustrate an embodiment of a sensor assembly 10 in which the pressure of a medical sensor 34 against the tissue may be adjusted. Illustrated in FIG. 6A is a side view of a headband-based sensor assembly 10 that includes an optical sensor 34 including an emitter 16 and a detector 18. The sensor assembly may include a strap or band 56 that may be fitted around a patient's forehead tissue 50 to contact the sensor 34 with the tissue 50. As shown, in certain embodiments in which the strap 56 is improperly fitted, the sensor 34 is not flush against the tissue 50. In such an embodiment, a pressure transducer 12 may send feedback to a downstream monitor about a lack of contact with the tissue 50. After receiving the feedback, the monitor may provide an indication or warning, after which a healthcare provide may inflate balloon 52 through inflation line 54. As shown in FIG. 6B, after inflation, the sensor 34 and the pressure transducer 12, which are positioned on the assembly 10 so that the inflation of the balloon pushes them towards the tissue 50, may be pressed flush against the forehead of the patient. The pressure sensor 12 may allow a user to adjust the pressure experienced by the patient to a range that is comfortable for the patient, and which does not significantly deform the underlying tissue and allows the sensor 34 to obtain accurate measurements.

Figure 8:
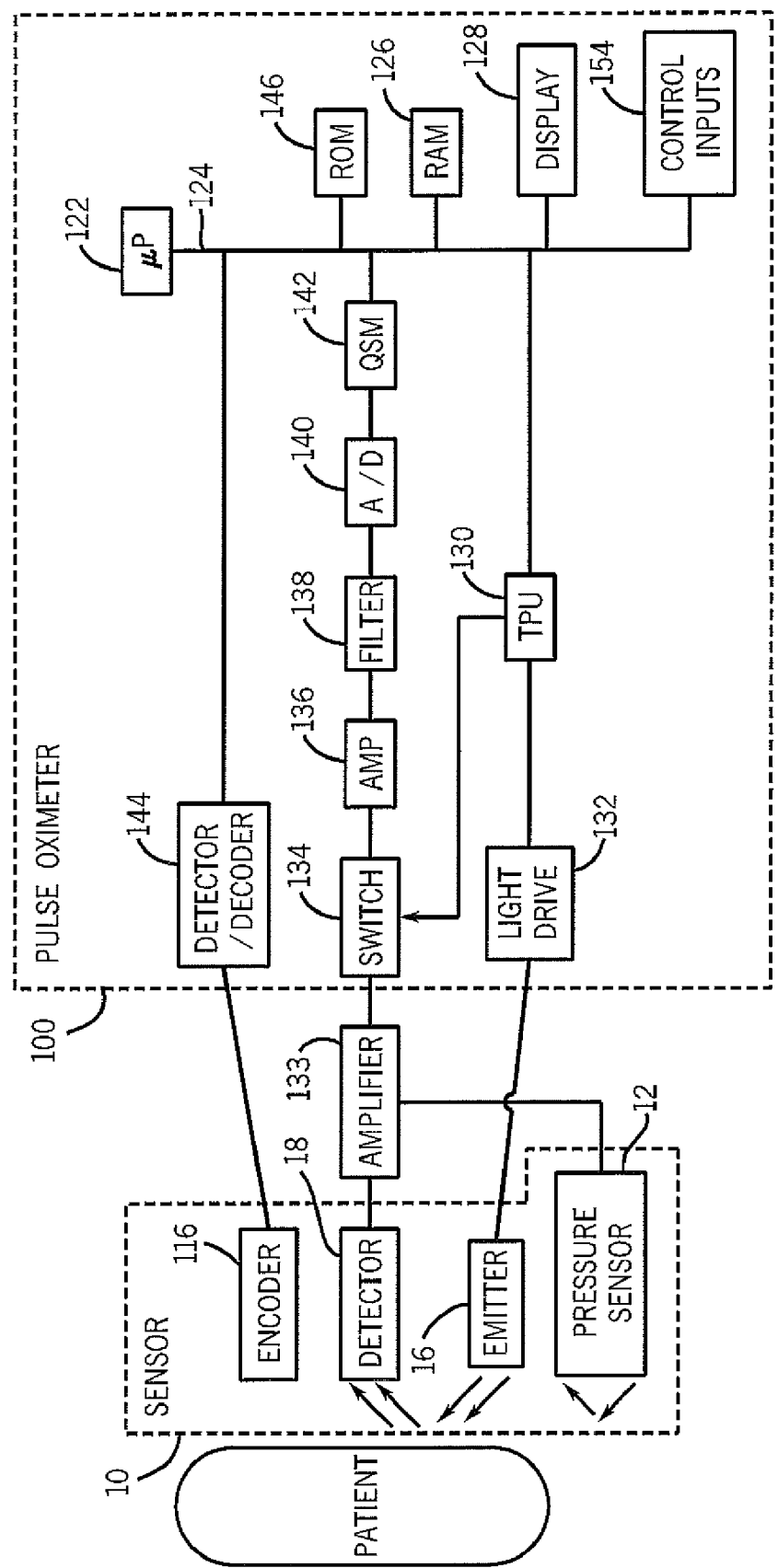
FIG. 8 is a block diagram of an exemplary pulse oximetry system.

A sensor or sensor assembly including pressure sensing and/or adjusting mechanisms as provided herein and illustrated generically as a sensor assembly 10, may be used in conjunction with a pulse oximetry monitor 100, as illustrated in FIG. 8. It should be appreciated that the cable 20 of the sensor assembly 10 may be coupled to the monitor 100 or it may be coupled to a transmission device (not shown) to facilitate wireless transmission between the sensor assembly 10 and the monitor 100. The monitor 100 may be any suitable pulse oximeter; such as those available from Nellcor Puritan Bennett LLC. Furthermore, to upgrade conventional pulse oximetry provided by the monitor 100 to provide additional functions, the monitor 100 may be coupled to a multi-parameter patient monitor 102 via a cable 104 connected to a sensor input port or via a cable 106 connected to a digital communication port.

FIG. 9 is a block diagram of an embodiment of a pulse oximeter 100 that may be configured to implement the embodiments of the present disclosure. Light from emitter 16 may pass into a blood perfused tissue, and may be scattered, and then detected by detector 18. A sensor assembly 10 containing an emitter 16 and a detector 18 may also contain an encoder 116 which may be capable of providing signals indicative of the wavelength(s) of light source 16 to allow the oximeter to select appropriate calibration coefficients for calculating oxygen saturation. The encoder 116 may, in an embodiment, be a resistor. In an embodiment, the sensor assembly 10 also includes a pressure sensor/transducer 12 and may be capable of carrying a signal from the pressure sensor 12 to a monitor 100.

In an embodiment, the sensor assembly 10 may be connected to a pulse oximetry monitor 100. The monitor 100 may include a microprocessor 122 coupled to an internal bus 124. Also connected to the bus may be a RAM memory 126 and a display 128. A time processing unit (TPU) 130 may provide timing control signals to light drive circuitry 132, which controls when the emitter 16 is activated, and if multiple light sources are used, the multiplexed timing for the different light sources. TPU 130 may also control the gating-in of signals from detector 18 through an amplifier 133 and a switching circuit 134. These signals are sampled at the proper time, depending at least in part upon which of multiple light sources is activated, if multiple light sources are used. The received signal from the detector 18 and the pressure sensor 12 may be passed through an amplifier 136, a low pass filter 138, and/or an analog-to-digital converter 140. The digital data may then be stored in a queued serial module (QSM) 142, for later downloading to RAM 126 as QSM 142 fills up. In an embodiment, there may be multiple parallel paths of separate amplifier, filter, and A/D converters for multiple light wavelengths or spectra received, and/or for the pressure data generated by the pressure sensor 12. In one embodiment, the signal from the pressure sensor 12 may be processed in any suitable manner, and may be sent through a different data path than the signal from the detector 18.

In an embodiment, the monitor 100 may be configured to receive signals from the sensor assembly 10. In certain embodiments, the monitor 100 may receive a signal from the pressure sensor 12 that indicates the magnitude of the pressure against the patient. The signals may be processed by the monitor 100 to indicate a sensor condition such as whether there is sufficient contact or insufficient contact. The monitor 100 may be configured to provide an indication about the sensor condition, such as an audio alarm, visual alarm or a display message, such as indicating the measured pressure. For example, in one embodiment, the pressure transducer may send a signal that the pressure is in the range of 16-40 mm Hg or 20-40 mm. In such an embodiment, the monitor 100 may provide a message "SUFFICIENT CONTACT," or may simply use a color indication, such as a green light, to indicate the sufficiency of the contact. In one embodiment, when the pressure is less than 16 mm Hg, the monitor 100 may provide a message "CONTACT LOW" or "CHECK SENSOR, or may provide a yellow or red indicator light. Further, the monitor 100 may be configured to receive information about the pressure sensor 12 from a memory chip or other device, such as the encoder 116, which may be on the sensor assembly 10 or the cable 20. In an embodiment, such a device may include a code or other identification parameter that may allow the monitor 100 to select an appropriate software or hardware instruction for processing the signal. In an embodiment, a monitor 100 may run an algorithm or code for processing the signal provided by the pressure sensor 12. In one embodiment, when the encoder 116 indicates that the sensor assembly 10 is configured for neonates, the pressure range for the sensor that is indicative of sufficient contact may be in the range of 16-40 mm Hg. In one embodiment, when the encoder 116 indicates that the sensor assembly 10 is configured for adults, the pressure range for the sensor that is indicative of sufficient contact may be in the range of 16-90 mm Hg, 20-40 mm Hg, or 60-90 mm Hg.

In an embodiment, the pressure transducer 12 may include one or more force-sensitive structures adapted to provide a signal relating to the pressure of the sensor 15 against the tissue. The pressure sensor 12 may be any appropriate sensor that is capable of converting a force applied to a sensor body into an electrical signal. In certain embodiments, the pressure sensor 12 may take the form of a displacement sensor. In one such embodiment, the pressure or force-sensitive structure may include a strain gauge or other mechanical displacement sensor. In another embodiment, the displacement sensor may include a linear variable differential transformer.

In other embodiments, a force-sensitive structure may be a resistance-based sensor. The pressure sensor 12 may include an array of electrodes, such as silver electrodes, printed as a matrix of intersecting rows and columns. An additional layer of semiconductive ink may provide an electrical resistance at each intersection on the matrix. Sandwiching these two layers together may create an array sensor. When a force is applied, the change in resistance is measured. Changing the formulation of the ink may produce different sensitivity ranges. Additionally, varying the spacing between rows and columns may yield finer resolution. In certain embodiments, a force-sensitive structure may have a spatial resolution, or sensor electrode spacing, of at least 0.0229 $mm^2$. An example of a pressure sensor 12 that is appropriate for use with a sensor 15 according to the present techniques is Flexiforce® film or flexible circuits, available from Tekscan (South Boston, Mass.).

In an embodiment, the pressure sensor 12 may also include polymers that are force-sensitive resistor materials. Force-sensitive resistor materials, such as those available from Interlink (Carptenteria, Ca.) and Advanced Composites Technology (Boston, Mass.) have a resistance variation under load. A force sensing resistor may be a piezoresistivity conductive polymer, which changes resistance in a predictable manner following application of force to its surface. It is normally supplied as a polymer sheet which has had the sensing film applied by screen printing. The sensing film typically includes both electrically conducting and non-conducting particles suspended in matrix. The particle sizes may be of the order of fraction of microns, and the particles may be formulated to reduce the temperature dependence, improve mechanical properties and increase surface durability. Applying a force to the surface of the sensing film causes particles to touch the conducting electrodes, changing the resistance of the film. Such a polymer-based force-sensitive resistor may be advantageous as it utilizes a relatively simple interface and can operate satisfactorily in moderately hostile environments.

In some embodiments, the pressure sensor 12 may take the form of a capacitance sensor. In such sensors, the capacitance is inversely proportional to the distance between the electrodes of the sensor. An exemplary capacitance-based sensor, TactArray, is available from Pressure Profile Systems (Los Angeles, Ca.). In certain embodiments, the capacitance sensor may be sensitive to forces or pressures from 1 psi to 200 psi.

In an embodiment the pressure sensor 12 may also include an elastomeric foam that is sensitive to force. The force-sensitive foam provides measurement of the resistance of a conductive elastomer or foam between two points. The force-sensitive foam may be a carbon doped rubber in which the resistance of the elastomer changes with the application of force, resulting from the deformation of the elastomer altering the particle density.

In an embodiment, based at least in part upon the received signals corresponding to the light received by detector 18, microprocessor 122 may calculate the oxygen saturation using various algorithms. These algorithms may require coefficients, which may be empirically determined, and may correspond to the wavelengths of light used. The algorithms may be stored in a ROM 146 and accessed and operated according to microprocessor 122 instructions.

In an embodiment of a two-wavelength system, the particular set of coefficients chosen for any pair of wavelength spectra may be determined by a value indicated by the encoder 116 corresponding to a particular light source in a particular sensor assembly 10. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

In an embodiment, the sensor assembly 10 includes an emitter 16 and a detector 18 that may be of any suitable type.

For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white lights" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects. For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra.

The emitter 16, the detector 18, and in some embodiments the pressure sensor 12, may be disposed on a sensor body 14, which may be made of any suitable material, such as plastic, foam, woven material, or paper. Alternatively, the emitter 16 and the detector 18 may be remotely located and optically coupled to the sensor assembly 10 using optical fibers. In the depicted embodiments, the sensor assembly 10 is coupled to a cable 20 that is responsible for transmitting signals from the pressure sensor 12 as well as electrical and/or optical signals to and from the emitter 16 and detector 18 of the sensor assembly 10. The cable 20 may be permanently coupled to the sensor assembly 10, or it may be removably coupled to the sensor assembly 10—the latter alternative being more useful and cost efficient in situations where the sensor assembly 10 is disposable.

In an embodiment, the sensor assembly 10 may include a "transmission type" sensor. Transmission type sensors include an emitter 16 and detector 18 that are typically placed on opposing sides of the sensor site. If the sensor site is a fingertip, for example, the sensor assembly 10 is positioned over the patient's fingertip such that the emitter 16 and detector 18 lie on either side of the patient's nail bed. In other words, the sensor assembly 10 is positioned so that the emitter 16 is located on the patient's fingernail and the detector 18 is located 180° opposite the emitter 16 on the patient's finger pad. During operation, the emitter 16 shines one or more wavelengths of light through the patient's fingertip and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor assembly 10 will perform in substantially the same manner.

Reflectance type sensors also operate by emitting light into the tissue and detecting the light that is transmitted and scattered by the tissue. However, reflectance type sensors include an emitter 16 and detector 18 that are typically placed on the same side of the sensor site. For example, a reflectance type sensor may be placed on a patient's fingertip or forehead such that the emitter 16 and detector 18 lie side-by-side. Reflectance type sensors detect light photons that are scattered back to the detector 18. A sensor assembly 10 may also be a "transflectance" sensor, such as a sensor that may subtend a portion of a baby's heel.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may to cover all modifications, equivalents, and alternatives falling within the spirit and scope of the disclosure as defined by the following appended claims

What is claimed is:

1. An apparatus comprising:
a headcovering capable of being applied to a patient's head;
a substrate disposed on the headcovering;
an emitter disposed on the substrate;
a detector disposed on the substrate;
a cable extending from the substrate through an open portion of the headcovering configured to be proximate to a top of the headcovering when the headcovering is applied to the patient; and
a pressure sensor associated with the headcovering, wherein the pressure sensor is capable of providing a pressure indication, and wherein the pressure sensor comprises a colorimetric film and a reference color strip.

2. The apparatus, as set forth in claim 1, wherein the pressure sensor is disposed on the substrate.

3. The apparatus, as set forth in claim 1, wherein the headcovering comprises a neonatal stocking cap.

4. The apparatus, as set forth in claim 1, comprising a tightening structure capable of increasing the pressure of the substrate against the patient's head.

5. The apparatus, as set forth in claim 1, wherein the headcovering comprises a plurality of indicia for openings such that when the openings are formed along the plurality of indicia, a pressure of the headcovering against the patient's head lessens.

6. The apparatus, as set forth in claim 5, wherein the indicia comprise slits or holes.

7. A pulse oximetry system comprising:
a pulse oximetry monitor; and
a sensor assembly capable of being operatively coupled to the monitor, the sensor assembly comprising:
a headcovering capable of being applied to a patient's head, wherein the headcovering comprises a plurality of indicia for openings such that when the openings are formed along the plurality of indicia, a pressure of the headcovering against the patient's head lessens;
a substrate disposed on the headcovering;
an emitter disposed on the substrate;
a detector disposed on the substrate;
a cable extending from the substrate through an open portion of the headcovering and configured to be proximate to a top of the headcovering when the headcovering is applied to the patient; and
a pressure sensor associated with the headcovering, wherein the pressure sensor is capable of providing a feedback to the monitor.

8. The system, as set forth in claim 7, wherein the feedback comprises an electrical signal.

9. The system, as set forth in claim 7, wherein the pressure sensor comprises a displacement-based sensor.

10. The system, as set forth in claim 7, wherein the pressure sensor comprises a colorimetric film.

11. The system, as set forth in claim 10, wherein the pressure sensor comprises a reference color strip.

12. The system, as set forth in claim 7, wherein the pressure sensor is disposed on the substrate.

13. The system, as set forth in claim 7, wherein the headcovering comprises a neonatal stocking cap.

14. The system, as set forth in claim 7, comprising a tightening structure capable of increasing the pressure of the substrate against the patient's head.

15. The system, as set forth in claim 7, wherein the monitor is capable of displaying an indication when the pressure is generally not in the range of 16 mm Hg-90 mm Hg.

16. The system, as set forth in claim 7, wherein the monitor is capable of displaying an indication when the pressure is generally not in the range of 20 mm Hg-40 mm Hg.

17. A method comprising:
emitting light into a tissue with an emitter;
detecting the light with a detector;
measuring a physiological characteristic based at least in part upon the detected light;
detecting a force experienced by at least one of the emitter and the detector with a force-sensitive sensor; and
adjusting the position of the emitter and the detector against the tissue with a headcovering comprising a plurality of indicia for openings when the force is outside of a predetermined range such that when the openings are formed along the plurality of indicia, the force lessens.

18. The method of claim 17, wherein the force-sensitive sensor comprises a colorimetric film and a reference color strip.

* * * * *